United States Patent
Perkins et al.

(10) Patent No.: US 8,292,807 B2
(45) Date of Patent: Oct. 23, 2012

(54) MOBILE MEDICAL WORKSTATION

(75) Inventors: David G. Perkins, Tully, NY (US);
Douglas J. Linquest, Fayetteville, NY (US); Thaddeus J. Wawro, Auburn, NY (US); Kristin A. Metz, Syracuse, NY (US); Peter H. Soderberg, Boca Grande, FL (US); Bonita L. Labosky, Minnetonka, MN (US); Robert L. Vivenzio, Auburn, NY (US)

(73) Assignee: Welch Allyn, Inc., Skaneateles Falls, NY (US)

( * ) Notice: Subject to any disclaimer, the term of this patent is extended or adjusted under 35 U.S.C. 154(b) by 0 days.

(21) Appl. No.: 12/873,765

(22) Filed: Sep. 1, 2010

(65) Prior Publication Data

US 2010/0324380 A1 Dec. 23, 2010

Related U.S. Application Data

(60) Division of application No. 11/131,015, filed on May 17, 2005, now abandoned, which is a continuation-in-part of application No. 10/643,487, filed on Aug. 19, 2003, now abandoned.

(60) Provisional application No. 60/404,601, filed on Aug. 20, 2002, provisional application No. 60/601,450, filed on Aug. 13, 2004, provisional application No. 60/658,626, filed on Mar. 4, 2005.

(51) Int. Cl.
*A61B 5/00* (2006.01)
*A61B 5/05* (2006.01)
*G09G 1/14* (2006.01)
*G08B 5/22* (2006.01)
*G08B 23/00* (2006.01)

(52) U.S. Cl. ..... 600/301; 600/365; 345/26; 340/286.07; 340/573.1

(58) Field of Classification Search ..... None
See application file for complete search history.

(56) References Cited

U.S. PATENT DOCUMENTS

| 4,785,969 | A | 11/1988 | McLaughlin |
| 4,911,167 | A * | 3/1990 | Corenman et al. ..... 600/324 |
| 5,014,875 | A | 5/1991 | McLaughlin et al. |
| 5,187,641 | A | 2/1993 | Muskatello et al. |
| D343,683 | S | 1/1994 | Muskatello et al. |
| 5,337,992 | A | 8/1994 | Pryor et al. |

(Continued)

FOREIGN PATENT DOCUMENTS

DE 102 11 365 A1 10/2003

(Continued)

OTHER PUBLICATIONS

European Search Report for EP Application No. 09010613.9; mailed Apr. 6, 2010; 6 pages.

*Primary Examiner* — Henry M Johnson, III
*Assistant Examiner* — Shirley Jian

(57) ABSTRACT

A medical workstation is defined by a supporting structure having at least one medical diagnostic instrument disposed thereupon. A first display is further disposed on a first side of the supporting structure and a second display is disposed on a second side of the supporting structure in a manner substantially opposite from the first display. Each of the first and second displays are interconnected to the at least one medical diagnostic instrument to permit at least one of the displays in order to display diagnostic results and are tandemly or independently controllable.

7 Claims, 24 Drawing Sheets

U.S. PATENT DOCUMENTS

| | | | |
|---|---|---|---|
| 5,355,149 A | 10/1994 | Casebolt | |
| 5,361,085 A | 11/1994 | Vance | |
| 5,375,604 A | 12/1994 | Kelly et al. | |
| D354,350 S | 1/1995 | Pryor et al. | |
| 5,474,574 A * | 12/1995 | Payne et al. | 607/7 |
| 5,537,289 A | 7/1996 | Dahl | |
| 5,590,648 A | 1/1997 | Mitchell et al. | |
| 5,640,953 A | 6/1997 | Bishop et al. | |
| 5,682,526 A | 10/1997 | Smokoff et al. | |
| 5,685,314 A | 11/1997 | Geheb et al. | |
| 5,687,717 A | 11/1997 | Halpern et al. | |
| 5,738,316 A | 4/1998 | Sweere et al. | |
| 5,752,917 A | 5/1998 | Fuchs | |
| 5,842,672 A | 12/1998 | Sweere et al. | |
| 5,865,733 A | 2/1999 | Malinouskas et al. | |
| 5,882,300 A | 3/1999 | Malinouskas et al. | |
| 5,939,699 A | 8/1999 | Perttunen et al. | |
| 5,947,907 A | 9/1999 | Duich | |
| 5,950,632 A | 9/1999 | Reber et al. | |
| 5,956,523 A | 9/1999 | Chen | |
| 6,003,006 A | 12/1999 | Colella et al. | |
| 6,003,072 A | 12/1999 | Gerritsen et al. | |
| 6,017,307 A | 1/2000 | Raines | |
| 6,035,328 A | 3/2000 | Soukal | |
| 6,076,166 A | 6/2000 | Moshfeghi et al. | |
| 6,116,461 A | 9/2000 | Broadfield et al. | |
| 6,171,237 B1 | 1/2001 | Avitall et al. | |
| 6,183,417 B1 | 2/2001 | Geheb et al. | |
| 6,202,360 B1 | 3/2001 | Rattner et al. | |
| 6,221,012 B1 | 4/2001 | Maschke et al. | |
| 6,285,742 B1 | 9/2001 | Haumann et al. | |
| 6,285,899 B1 | 9/2001 | Ghaem et al. | |
| 6,289,238 B1 | 9/2001 | Besson et al. | |
| 6,317,719 B1 | 11/2001 | Schrier et al. | |
| 6,338,007 B1 | 1/2002 | Broadfield et al. | |
| 6,338,714 B1 | 1/2002 | Krause et al. | |
| 6,339,410 B1 | 1/2002 | Milner et al. | 600/300 |
| 6,339,732 B1 | 1/2002 | Phoon et al. | |
| 6,343,601 B1 | 2/2002 | Kiske et al. | |
| 6,348,793 B1 | 2/2002 | Balloni et al. | |
| 6,352,504 B1 | 3/2002 | Ise et al. | |
| 6,354,996 B1 | 3/2002 | Drinan et al. | |
| D455,916 S | 4/2002 | Fluhrer et al. | |
| D456,171 S | 4/2002 | Coonan et al. | |
| 6,377,162 B1 | 4/2002 | Delestienne et al. | |
| 6,394,402 B2 | 5/2002 | Coonan et al. | |
| 6,405,165 B1 | 6/2002 | Blum et al. | |
| D459,610 S | 7/2002 | Coonan et al. | |
| 6,427,167 B1 | 7/2002 | Siedel | |
| 6,441,747 B1 | 8/2002 | Khair et al. | |
| 6,450,966 B1 | 9/2002 | Hanna | |
| 6,463,320 B1 | 10/2002 | Xue et al. | |
| 6,478,736 B1 | 11/2002 | Mault | |
| D466,721 S | 12/2002 | Coonan et al. | |
| 6,493,220 B1 | 12/2002 | Clark et al. | |
| 6,520,910 B1 | 2/2003 | Kohls | |
| 6,551,243 B2 | 4/2003 | Bocionek et al. | |
| 6,568,596 B1 | 5/2003 | Shaw | |
| 6,575,900 B1 | 6/2003 | Zweig et al. | |
| 6,577,893 B1 | 6/2003 | Besson et al. | |
| 6,579,241 B2 | 6/2003 | Roeher | |
| 6,581,069 B1 | 6/2003 | Robinson et al. | |
| 6,584,454 B1 | 6/2003 | Hummel, Jr. et al. | |
| 6,585,645 B2 | 7/2003 | Hutchinson | |
| 6,585,731 B1 | 7/2003 | Rattner | |
| 6,587,945 B1 | 7/2003 | Pasieka | |
| 6,589,170 B1 | 7/2003 | Flach et al. | |
| 6,594,146 B2 | 7/2003 | Frangesch et al. | |
| 6,601,172 B1 | 7/2003 | Epstein | |
| 6,603,494 B1 | 8/2003 | Banks et al. | |
| 6,603,991 B1 | 8/2003 | Karmalawy et al. | |
| 6,607,485 B2 | 8/2003 | Bardy | |
| 6,609,016 B1 * | 8/2003 | Lynn | 600/323 |
| 6,609,115 B1 | 8/2003 | Mehring et al. | |
| 6,612,664 B2 | 9/2003 | Pryor et al. | |
| 6,988,989 B2 | 1/2006 | Weiner et al. | |
| 7,154,397 B2 | 12/2006 | Zerhusen et al. | 600/300 |
| 7,587,354 B2 * | 9/2009 | Parsons et al. | 705/37 |
| 7,668,579 B2 * | 2/2010 | Lynn | 600/323 |
| 8,187,201 B2 * | 5/2012 | Lynn | 600/538 |
| 2002/0002473 A1 | 1/2002 | Schrier et al. | |
| 2002/0087054 A1 | 7/2002 | Lin et al. | |
| 2002/0093537 A1 | 7/2002 | Bocioned et al. | |
| 2002/0095315 A1 | 7/2002 | Redel | |
| 2002/0099274 A1 | 7/2002 | Isomura et al. | |
| 2002/0106709 A1 | 8/2002 | Potts et al. | |
| 2002/0158911 A1 | 10/2002 | O'Rourke | |
| 2002/0158912 A1 | 10/2002 | O'Rourke | |
| 2002/0161795 A1 | 10/2002 | O'Rourke | |
| 2002/0184568 A1 | 12/2002 | Kurrasch | |
| 2003/0009106 A1 | 1/2003 | Sitzman et al. | |
| 2003/0018185 A1 | 1/2003 | Havukkala et al. | |
| 2003/0018241 A1 * | 1/2003 | Mannheimer | 600/300 |
| 2003/0050792 A1 | 3/2003 | Shiraishi | |
| 2003/0065805 A1 * | 4/2003 | Barnes, Jr. | 709/231 |
| 2003/0074220 A1 | 4/2003 | Brandt | |
| 2003/0076925 A1 | 4/2003 | DeSilets et al. | |
| 2003/0092980 A1 | 5/2003 | Nitz | |
| 2003/0105389 A1 | 6/2003 | Noonan et al. | |
| 2003/0119445 A1 | 6/2003 | Bromham et al. | |
| 2003/0120652 A1 | 6/2003 | Tifft | |
| 2003/0125987 A1 | 7/2003 | Rucker | |
| 2003/0125988 A1 | 7/2003 | Rao et al. | |
| 2003/0144590 A1 | 7/2003 | Maschke | |
| 2003/0158466 A1 * | 8/2003 | Lynn et al. | 600/300 |
| 2003/0172151 A1 | 9/2003 | Schade | |
| 2006/0276695 A9 * | 12/2006 | Lynn et al. | 600/300 |

FOREIGN PATENT DOCUMENTS

| | | |
|---|---|---|
| DE | 10211365 A1 | 10/2003 |
| EP | 0 310 699 A1 | 4/1989 |
| WO | WO 98/55021 | 12/1998 |
| WO | 01/86575 A2 | 11/2001 |
| WO | WO-0186575 A2 | 11/2001 |
| WO | 02/33681 A2 | 4/2002 |
| WO | 2004/017831 A1 | 3/2004 |
| WO | WO-2004/017831 A1 | 3/2004 |

* cited by examiner

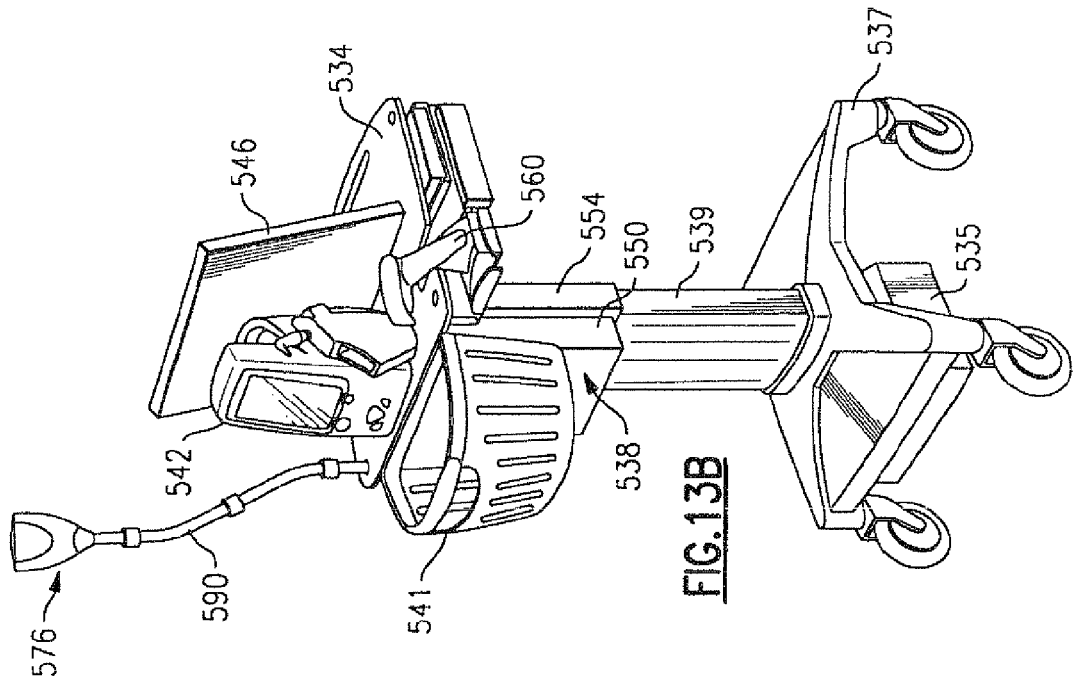
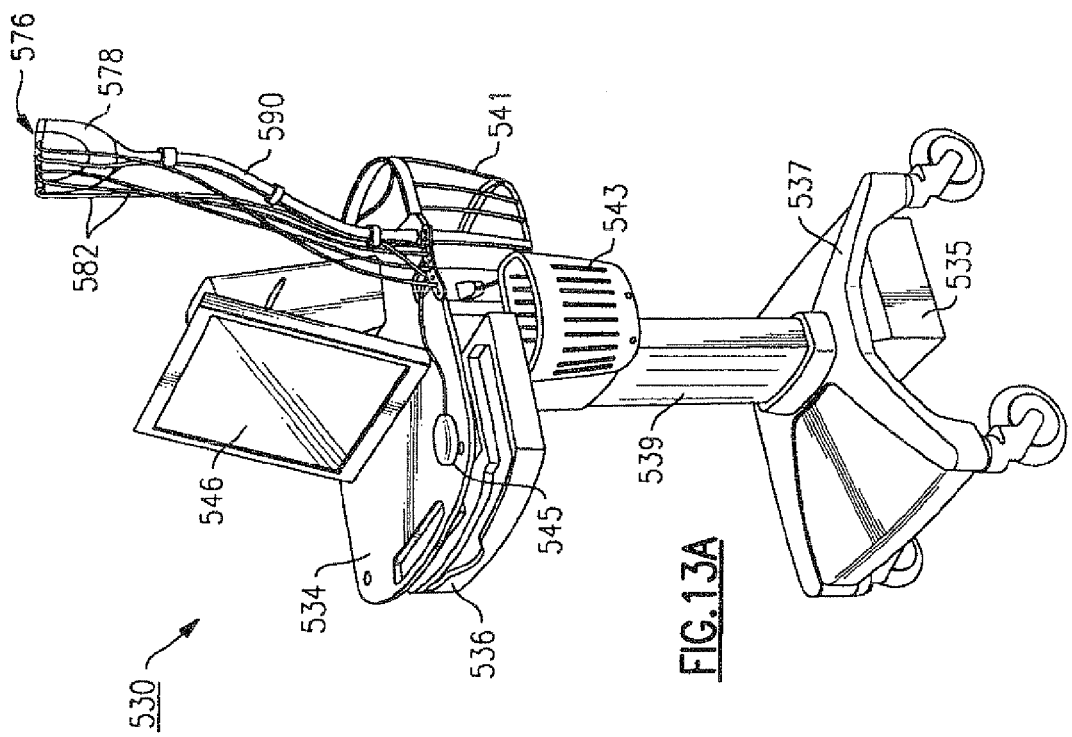

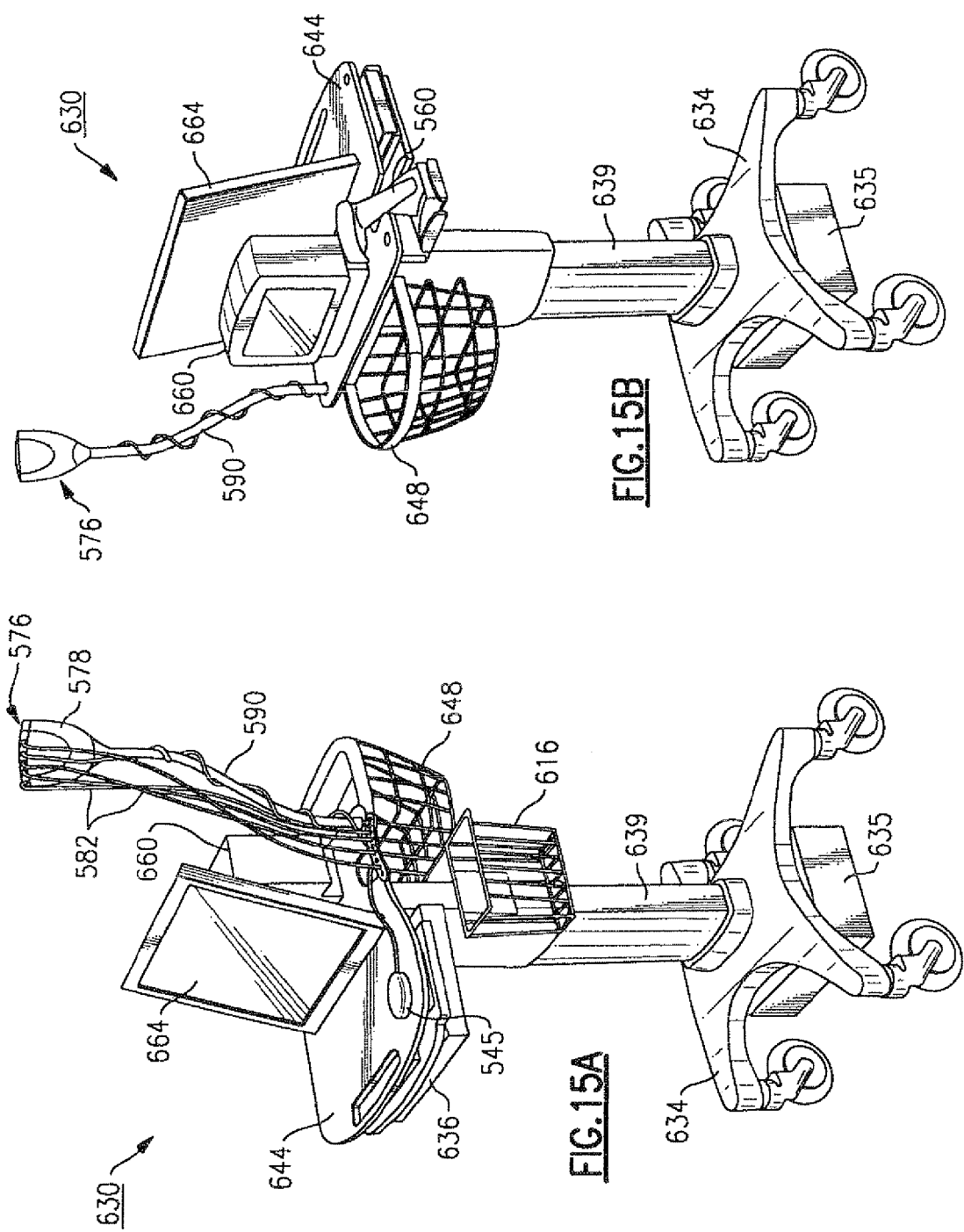

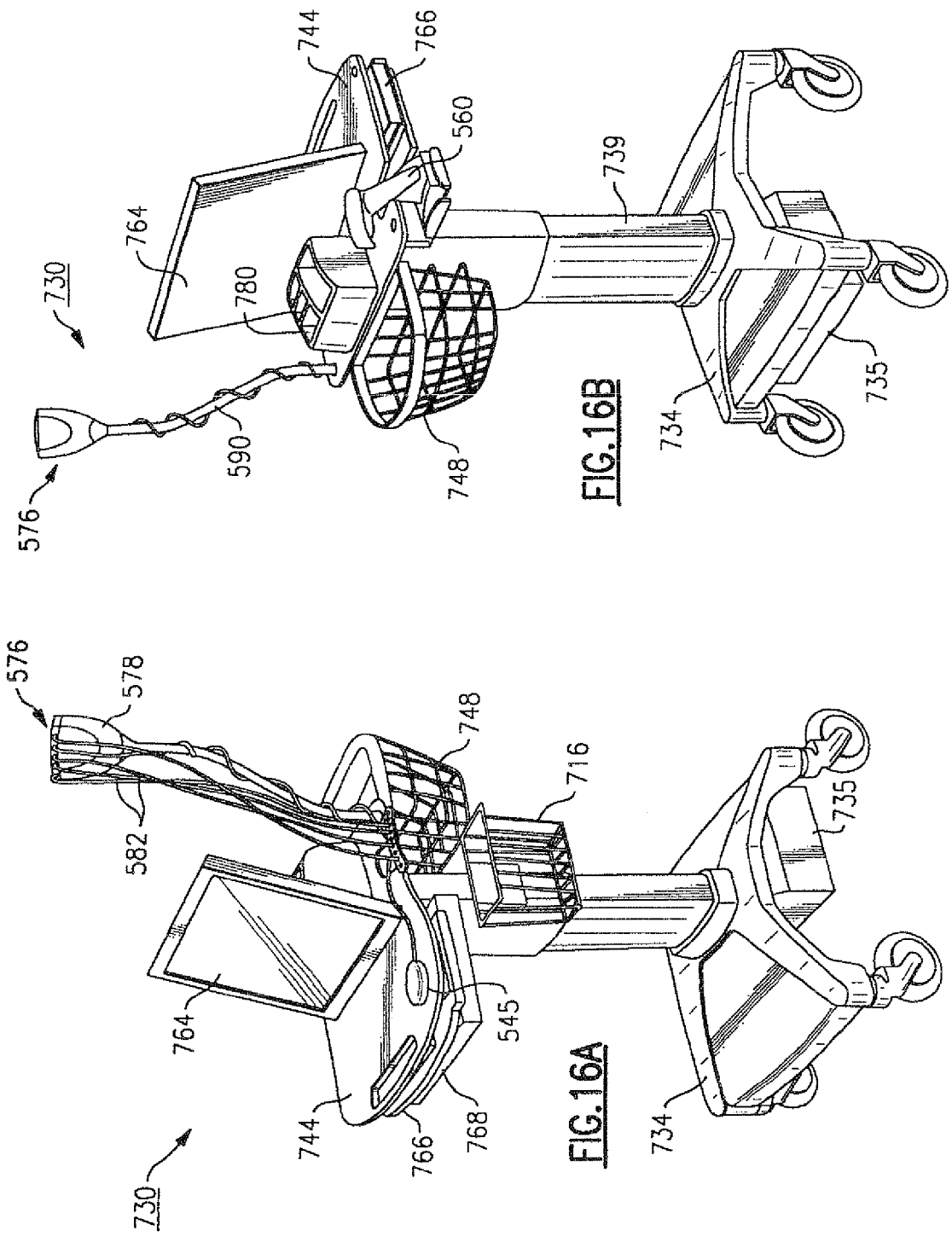

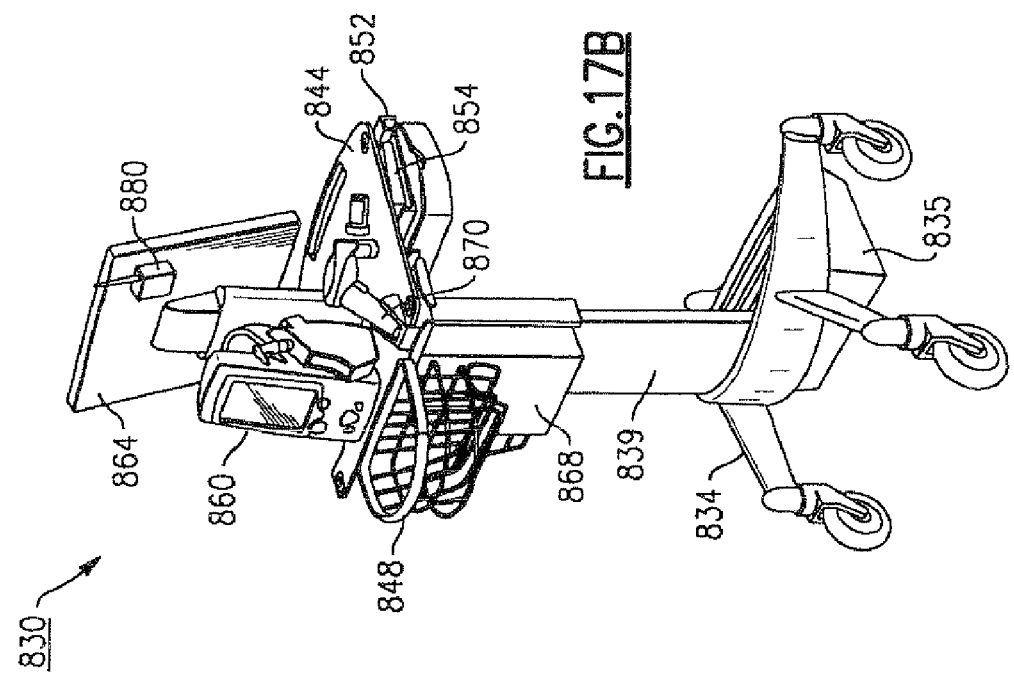
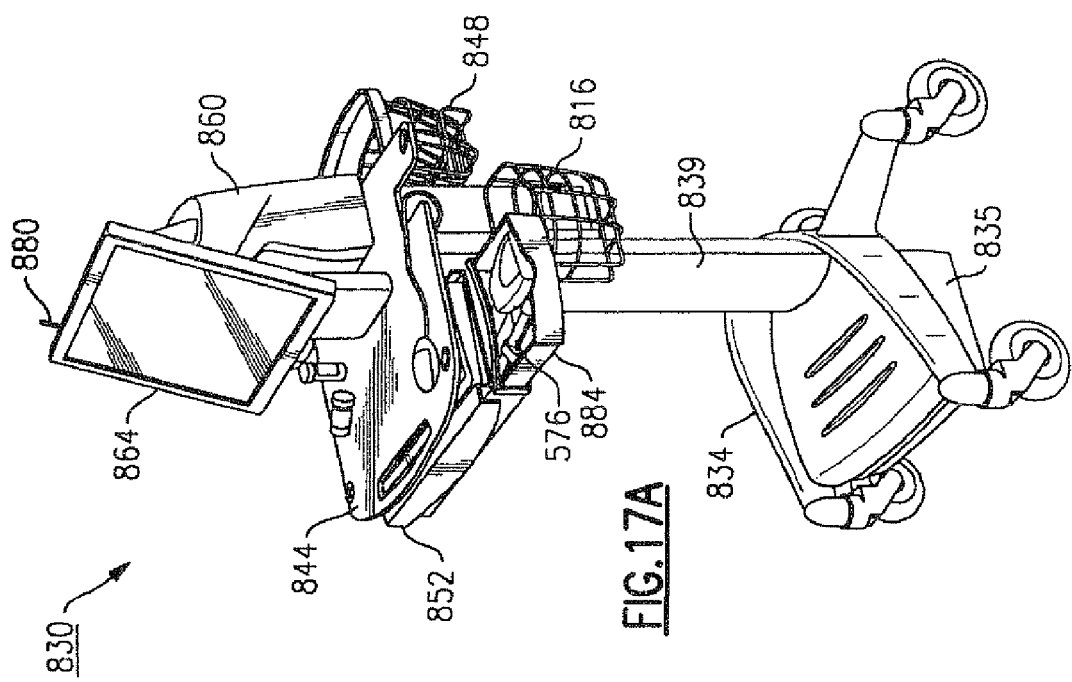

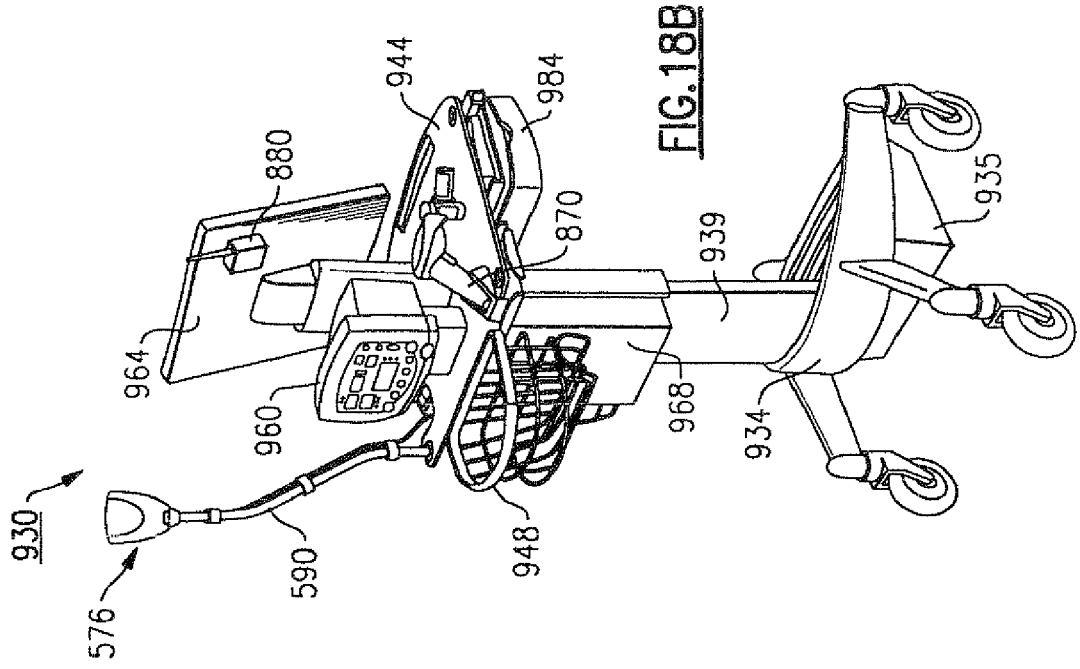
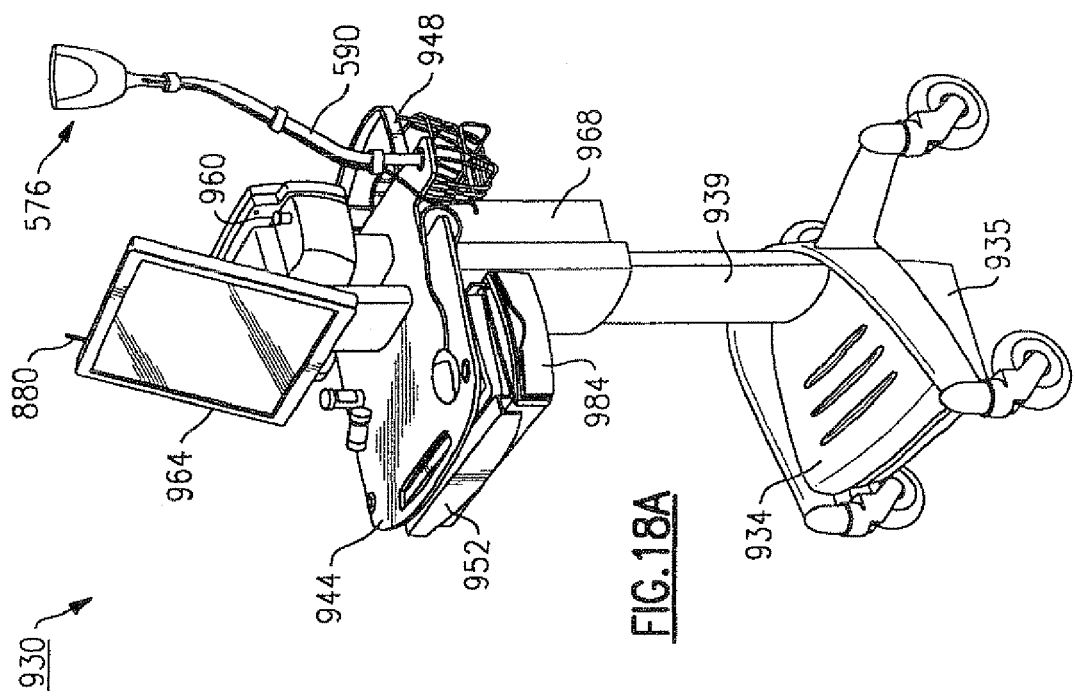

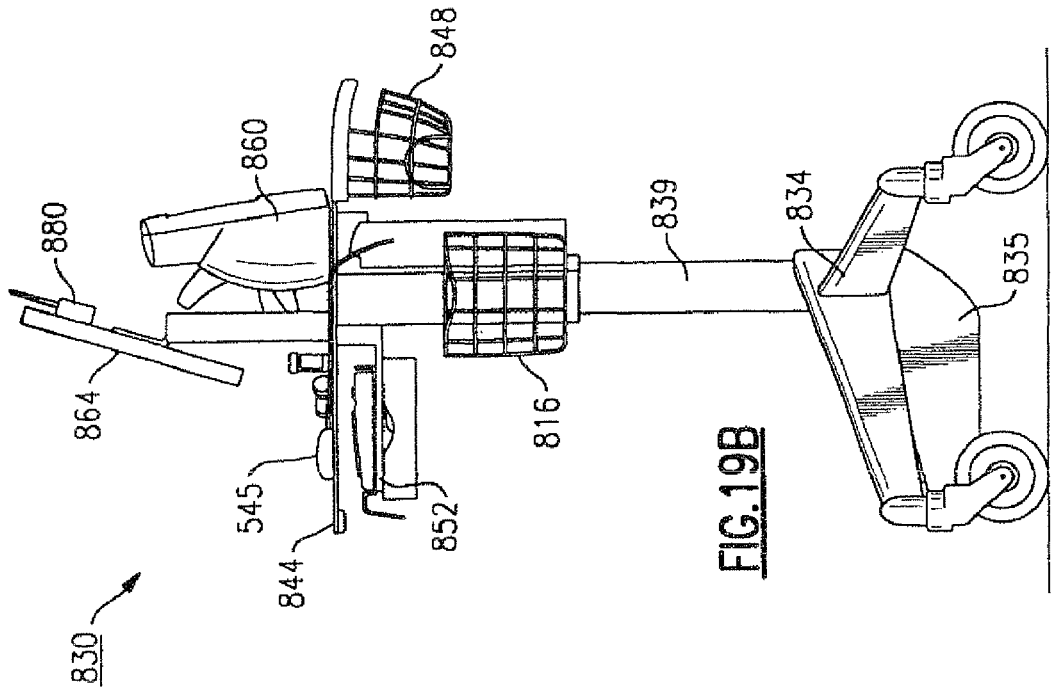
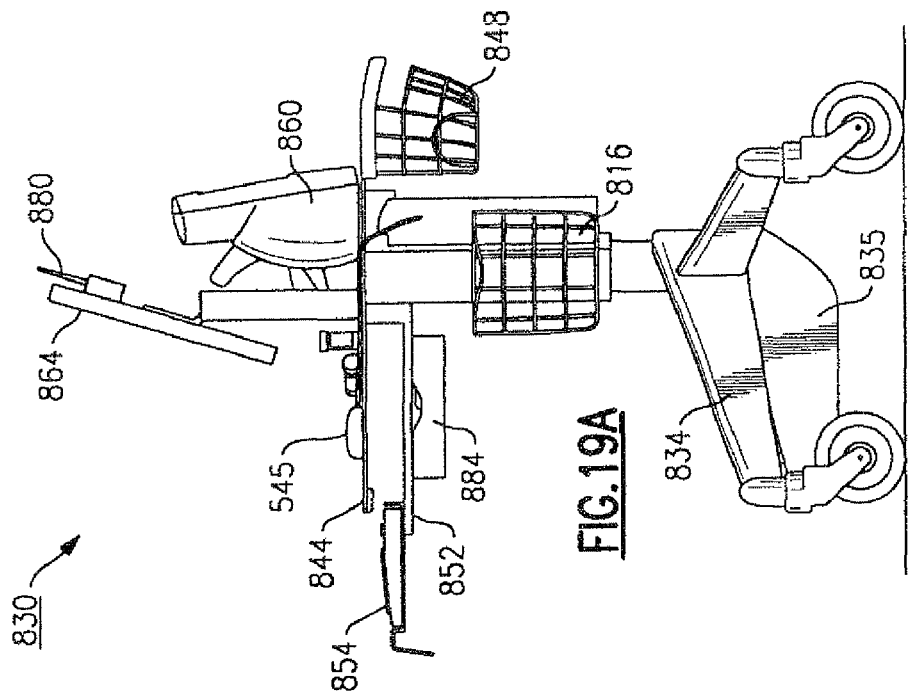

MOBILE MEDICAL WORKSTATION

CROSS REFERENCE TO RELATED APPLICATIONS

This patent application is a divisional application of U.S. Ser. No. 11/131,015, filed May 17, 2005, which claims priority based upon U.S. Ser. No. 60/658,626, entitled: MOBILE MEDICAL WORKSTATION, filed Mar. 4, 2005, and U.S. Ser. No. 60/601,450, entitled: MOBILE MEDICAL WORKSTATION, filed Aug. 13, 2004, the entire contents of which are herein incorporated by reference in their entirety. This application is also a continuation-in-part application of U.S. Ser. No. 10/643,487, entitled: DIAGNOSTIC INSTRUMENT WORKSTATION, filed Aug. 19, 2003 (now abandoned), which is based upon U.S. Ser. No. 60/404,601, filed Aug. 20, 2002, the entire contents of each being herein incorporated by reference. This patent application further incorporates by reference the entirety of commonly owned and U.S. Ser. No. 11/032,625 (now abandoned), entitled "A PORTABLE VITAL SIGNS MEASUREMENT INSTRUMENT AND METHOD OF USE THEREOF", filed Jan. 10, 2005, and U.S. Pat. No. 7,429,245, filed Jul. 14, 2003 and entitled: MOTION MANAGEMENT IN A BLOOD PRESSURE MEASUREMENT DEVICE", each of the preceding being subject to assignment to the common assignee of the present application.

FIELD OF THE INVENTION

This relates to the field of diagnostic medicine and more particularly to a mobile medical diagnostic workstation used in connection with at least one patient for measuring and storing a number of physiologic parameters.

BACKGROUND OF THE INVENTION

The staff of a medical/surgical floor of a typical hospital is under an increasing amount of pressure. Contributing to these pressures is the pervasive nursing shortage that has translated into a lower nurse to patient ratio, with longer hours and increased overtime. As a result, errors due to oversight and the like are likely to increase. Formerly, patient vital signs data were taken by a registered nurse (RN), but now these readings are often taken numerous times per day (as many as six or more readings) by nursing aides (also referred to as Patient Care Technicians (PCTs)) who must cover more patients and often have no or little clinical training. In addition and in an effort to ease the above staffing strains, many hospitals utilize more temporary contract or "traveler" nurses who float between sites. As a result, users of the monitoring equipment are transitory and must learn new internal procedures very quickly, exacerbating the above problems.

Currently, PCTs often use a cart having a number of patient diagnostic devices that can include automated blood pressure, thermometry, and pulse oximetry apparatus used to take patient vital signs over a length of stay. As noted, a PCT may likely take six readings (or more) per day over an average hospital stay of about five days. Typically, the above devices are not integrated on a cart, but rather are arranged in a piecemeal fashion, though integrated vital sign monitoring (VSM) devices, such as those manufactured by Welch Allyn, Inc. of Skaneateles Falls, N.Y. are commonly known in the field.

Vital sign readings, when taken, are often written onto a loose worksheet or often onto scraps of paper. At the end of rounds, these readings are then copied onto the patient's chart on a "vitals" sheet. If anomalous readings are detected, the RN is notified. Otherwise, the RN is usually not consulted and often will not or may not get the chance to review any of the readings which have been taken.

Upon examination and if the vital signs readings are suspect in any way, the RN will often send the PCT back to the patient and request that another reading(s be taken. In the meantime, even if a significant change in the patient's vitals has been detected, time has been wasted and therefore lost. It is possible that in the current manner of testing described above, that many vital signs variations are not caught or otherwise detected or noted until the patient's condition has significantly changed.

Though the problems are arguably less involved, there are similar generalized needs in other clinical settings, such as the physician's offices, in order to be able to better conduct and document patient clinical encounters more efficiently and with better accuracy.

SUMMARY OF THE INVENTION

It is therefore one object of the present invention to improve upon the above-noted deficiencies of the prior art.

It is another object of the present invention to improve the manner of conducting patient clinical encounters, whether in a doctor's office and/or in the hospital environment.

It is yet another object of the present invention to provide an integrated medical diagnostic workstation that provides simple, efficient and improved operation for both the patient and the user(s) whether the user is a nurse, nursing aide, clinician or doctor.

It is another object of the present invention to facilitate the flow of information between caregivers.

It is yet another object of the present invention to be able to integrate general computing technology into the workflow of patient encounters along with the use of medical devices, thereby permitting applications, such as electronic medical records (EMRs) and/or medication delivery applications, to be utilized.

It is yet another object of the present invention to be able to integrate equipment within a workstation that optimizes workspace; that is, permitting various procedures to be performed effectively while maintaining a convenient footprint wherein the workstation is suitably rugged and stable to permit reliable use in a number ° C. varied environments.

Therefore and according to an aspect of the present invention, there is provided a medical workstation comprising a supporting structure, at least one medical diagnostic instrument disposed on the supporting structure, a first display disposed on a first side of said supporting structure, and a second display disposed on a second side of said supporting structure substantially opposite from said first side. Each of the first and second displays are interconnected to the at least one medical diagnostic instrument to permit at least one of said displays to display diagnostic results.

Preferably, the at least one medical diagnostic instrument is a vital signs device having the first display integrated therein. A computing device, such as a tablet PC, is also preferably included and is supported by the herein described workstation, the PC being attached to the second side of the supporting structure and having the second display. A docking station is preferably provided for the PC on the workstation to supply power and provide interconnection with the at least one medical diagnostic instrument using either a wired or wireless connection.

Preferably, at least one of the displays is adjustable about a horizontal axis in order to permit likability thereof relative to the user. Additionally, the height of the devices and a horizontal work surface can also selectively be adjusted as needed.

According to one variation, the devices are removable to permit their use either with the workstation or as free standing. Alternatively, free standing devices can also be integrated with the workstation according to another version thereof.

Moreover, the workstation includes control means to selectively control the operation of at least one aspect of the workstation including selective control of the first and second displays. The control means can either be included within the vital signs measuring device, the PC, or separately such as through another device or via a network.

For example, at least one input device can also be provided, such as a keyboard. a mouse, a touchscreen, or an automatic identification and data collection device, such as a bar code scanner, that is interconnected to at least one of the at least one medical diagnostic instrument and the PC. The at least one input device can also be used as a control means for the workstation and provide remote control of either display and/ or the medical diagnostic instrument to cause automated vital readings to be taken, for example. Additionally, the at least one input device permits manual input of certain parameters, such as patient demographics and/or patient qualifiers (e.g., whether the patient is sitting or prone, the last meal prior to a glucose reading, and/or other information having a bearing on a particular measurement). Moreover, the control means can control the amount of data being presented on either display, for example, the control means can selectively remove certain data from one of the displays for security or other reasons or can disable the function of one or both displays, as needed.

In the instance in which the input device is an AIDC scanning device, such as a 1D or 2D bar code scanner, the device can be provided, according to one version, as a presentation scanner that is oriented on the work surface of the workstation. In this manner, it is not required to manually remove the scanner each time that it is desired to obtain information, such as a patient record, medication information, or other data. As such, the data can simply be brought to a scanning station.

According to another aspect of the present invention, there is provided a method for manufacturing a mobile medical workstation, said method comprising the steps of:

supporting a first display on said workstation, said first display facing a first side of said workstation; and supporting a second display on said workstation, said second display facing a second side of said workstation and oppositely from said first display wherein each of said first and said second displays are connected to at least one medical diagnostic instrument such that each said display is capable of displaying results of said at least one medical diagnostic instrument.

According to yet another aspect of the present invention, there is described an integrated apparatus for use in a patient encounter, and in which the apparatus comprises: at least one medical diagnostic instrument, including a vital signs device having a sphygmomanometer; and a computing device connected to the at least one medical diagnostic instrument, said computing device including means for determining the size of the cuff of the sphygmomanometer utilized.

According to yet another aspect of the present invention, there is provided an integrated apparatus for use in a patient encounter. The apparatus according to this aspect comprises at least one medical diagnostic instrument, including a vital signs device and a sphygmomanometer; and a computing device connected to at least one medical diagnostic instrument, wherein said sphygmomanometer includes an inflatable sleeve having a pressure control assembly for inflating and deflating said sleeve, said pressure control assembly being connected to said computing device so as to inflate the sleeve to a predetermined pressure depending on the patient whose blood pressure is being measured.

According to yet another aspect of the present invention, there is provided an integrated apparatus for use in a patient encounter. The apparatus comprises at least one medical diagnostic instrument including a vital signs device for measuring various physiological parameters of a said patient; and a computing device connected to said at least one medical diagnostic instrument, wherein at least one of said computing device and said at least one medical diagnostic instrument are programmed to detect changes in a patient condition based on changes in measured parameters.

According to still another aspect of the present invention, there is provided an integrated apparatus for use in a patient encounter. The apparatus comprises at least one medical diagnostic instrument, including a vital signs device; and a computing device connected to at least one medical diagnostic instrument for measuring a physiologic parameter of a patient, wherein said at least one medical diagnostic instrument further includes a portable EKG assembly.

In one version, the EKG monitoring assembly is connected to the computing device.

According to still another version of the present invention, there is provided an integrated apparatus for use in a patient encounter. The apparatus comprises at least one medical diagnostic instrument, including a vital signs device; an input device having means for reading machine-readable information; and a computing device connected to at least one medical diagnostic instrument and said input device, said apparatus further including means for determining the amount of fluid inputs and outputs of a patient.

According to still another version of the present invention, there is provided an integrated apparatus for use in a patient encounter. The apparatus comprises at least one medical diagnostic instrument, including a vital signs device; and a computing device connected to at least one medical diagnostic instrument, wherein at least one of said computing device and said at least one medical diagnostic instrument include memory means that includes means for storing at least audio data added during said patient encounter.

At least one audio message can be transmitted by the workstation to a remote location and/or the audio message can be played back at the workstation. The latter is a preferred means for handling coordination of a patient between shifts wherein pertinent notes concerning the patient can be left for playback by the oncoming attending shift nurse or aide. Text messages providing pertinent or updated patient information or notes, can also be left for subsequent users on the workstation, in addition to the audio notes.

In the instance of transmitting the at least one audio message remotely, the computing device can be connected to the remote location by way of a bidirectional communication link. This link can be a wireless or a wired link or can include a WiFi or other Internet connection for transmission of the audio data, for example, by means of .audio files. Alternately, the workstation can include a speakerphone using VOIP for receiving audio messages to and from the remote location.

According to still another version of the present invention, there is provided an integrated apparatus for use in a patient encounter, the apparatus comprising at least one medical diagnostic instrument, including a vital signs device; means for selectively capturing images during a patient encounter; and a computing device connected to said at least one medical diagnostic instrument and said image capture means.

In this version, the computing device can include a display and the apparatus can include means for displaying an image of a user that is logged onto the apparatus. This image capturing means can, for example, be an imaging bar code scanning device wherein the apparatus further includes means for preventing unauthorized access to or operation of the herein described apparatus. In one version, this biometric means can include memory means that includes storage of images of authorized users of the apparatus and in which operation of the apparatus can occur only if a successful comparison between a stored image and that of the user are attained.

According to still another version of the present invention, there is provided an integrated apparatus for use in a patient encounter, the apparatus comprising at least one medical diagnostic instrument, including a vital signs device; and a computing device connected to at least one medical diagnostic instrument, at least one of said computing device and said vital signs device including a graphical display wherein said display includes a graphical user interface, said graphical user interface including a body image format permitting a user to readily identify the patient physiological parameters being measured.

In one version, the body image format includes a body representation wherein physiological parameter readings of a monitored patient are disposed in proximity to the actual location on the body that is being measured.

The user interface provides visual indications of regions that are currently being measured or provides a user with the information concerning areas or regions that are not being measured in connection with the patient. The visual indication can include highlighting or other forms of notification or indication of out of range readings. The interface permits both current and trended data to be displayed.

According to yet another aspect of the present invention, there is provided a medical workstation comprising a supporting structure; at least one medical diagnostic instrument disposed on said supporting structure; and a computing device disposed on said supporting structure, said supporting structure being mobile and including a wheeled chassis permitting said workstation to be mobile and in which said supporting structure is foldable to permit storage thereof.

In one version thereof, the supporting structure includes a movable upper portion supporting the at least one medical diagnostic instrument and the computing device, wherein the apparatus further includes adjustment means for selectively adjusting the height of the upper portion relative to the remainder of the supporting structure.

An advantage of the present invention in providing dual displays on the workstation is that displayed results can be presented simultaneously to both the patient and to the user, providing redundancy for example, in the event one of the displays is not visible from the caretaker's current location.

Another advantage provided is that the herein described mobile workstation improves response time and provides ease of use for all users, whether PCTs, RNs, doctors, clinicians or others.

Still another advantage provided by the present invention is that the at least one medical diagnostic instrument can be controlled for either automated and/or manual taking of patient vitals wherein the results can be automatically logged without requiring transcription, thereby improving time, efficiency and accuracy. Moreover, the data can be stored for trend analysis and alerts can be created automatically to permit additional readings to be taken if a patient's condition changes significantly.

Yet another advantage is that each of the displays can be separately controlled in order to select which information is shown on each display for ease of use and for security/privacy (HIPAA) concerns. For example, the user could utilize the controls of the medical diagnostic instrument when the user is on that side of the workstation, and disable the computer display. When the user is on the computer side of the workstation, the display of the at least one medical diagnostic instrument can be caused to dim or turned off to protect patient confidential information. In fact, the user could operate the at least one medical device from the computer without requiring the instrument display, selectively.

Another advantage of the present workstation is the utilization of a docking station for the computer and/or at least one medical diagnostic instrument, permitting the devices to be utilized separate from the workstation. For example, some patients are isolated for contagious diseases—a dockable vitals device allows them to bring only the device into the patient's room, to simplify decontamination later. Further, nurses may want to remove the computer to complete documentation in areas where a wheeled cart may not be optimal, such as, for example, a breakroom.

These and other objects, features, and advantages will become readily apparent from the following Detailed Description which should be read in conjunction with the accompanying drawings.

BRIEF DESCRIPTION OF THE DRAWINGS

FIG. 13A is a front perspective view of a mobile medical workstation in accordance with a second embodiment of the present invention;

FIG. 13B is a rear perspective view of the mobile medical workstation of FIG. 13A;

FIG. 15A is a front perspective view of a mobile medical workstation in accordance with a third embodiment of the present invention;

FIG. 15B is a rear perspective view of the mobile medical workstation of FIG. 15A;

FIG. 16A is a front perspective view of a mobile medical workstation in accordance with a fourth embodiment of the present invention;

FIG. 16B is a rear perspective view of the mobile medical workstation of FIG. 16A;

FIG. 17A is a front perspective view of a mobile medical workstation in accordance with a fifth embodiment of the present invention;

FIG. 17B is a rear perspective view of the mobile medical workstation of FIG. 17A;

FIG. 18A is a front perspective view of a mobile medical workstation in accordance with a sixth embodiment of the present invention; and FIG. 18B is a rear perspective view of the mobile medical workstation of FIG. 18A;

FIGS. 19A and B are side views of the mobile medical workstation of FIGS. 17A and B, respectively;

DETAILED DESCRIPTION

Figure 1:
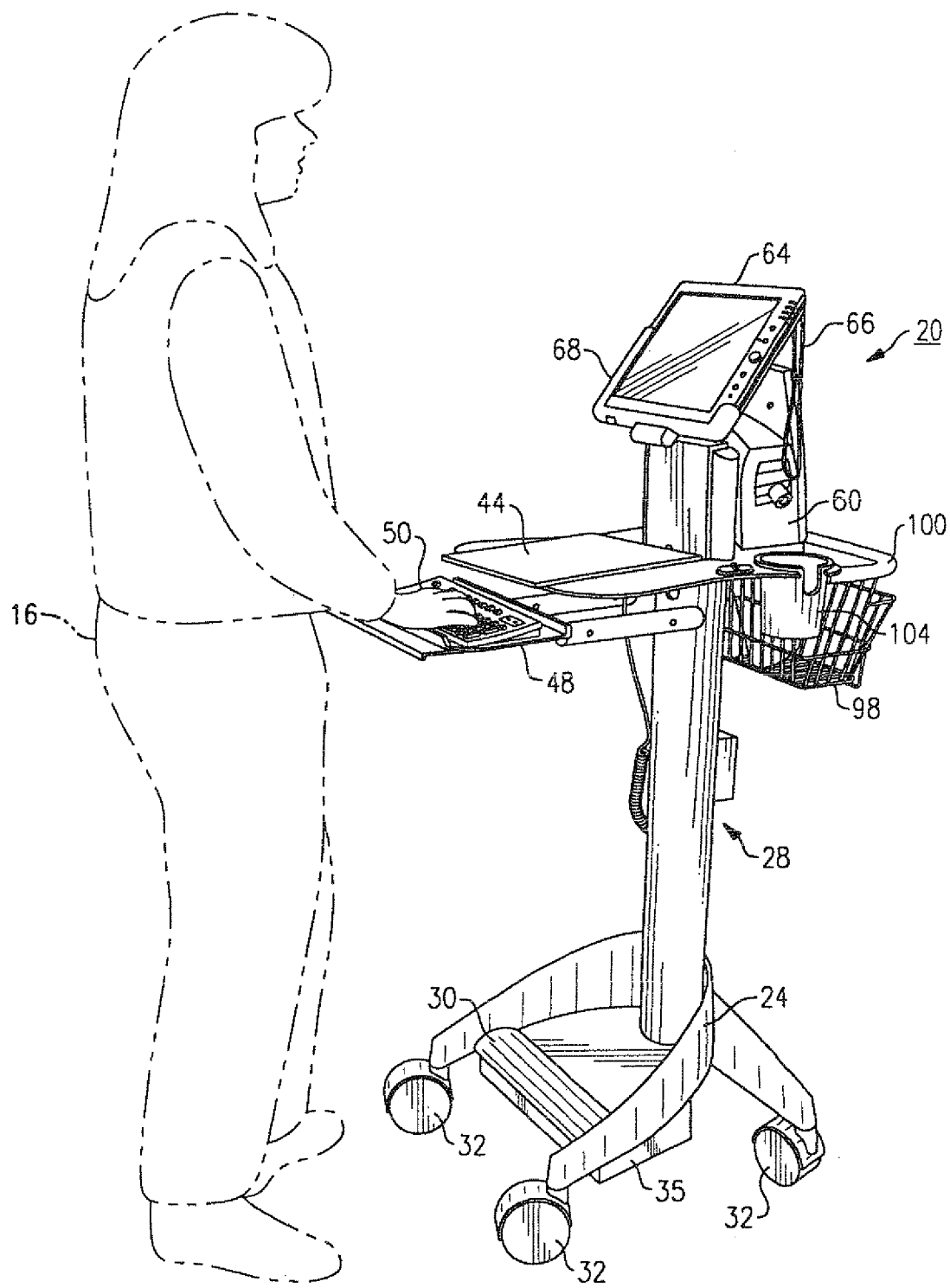
FIG. 1 is a side perspective view of a mobile medical workstation made in accordance with a preferred embodiment of the present invention as shown in a use environment.
Figure 2:
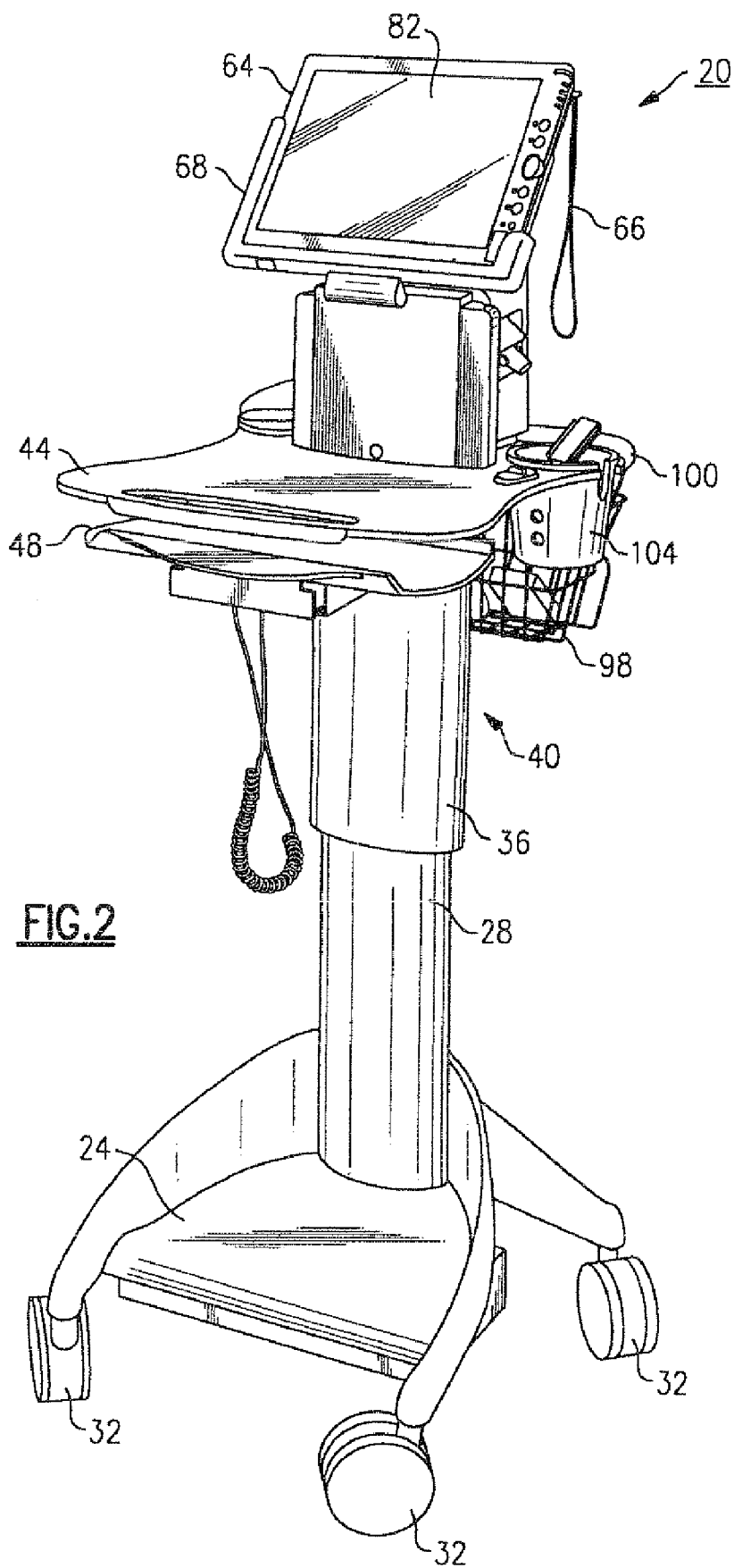
FIG. 2 is a front perspective view of the mobile medical workstation of FIG. 1.
Figure 3:
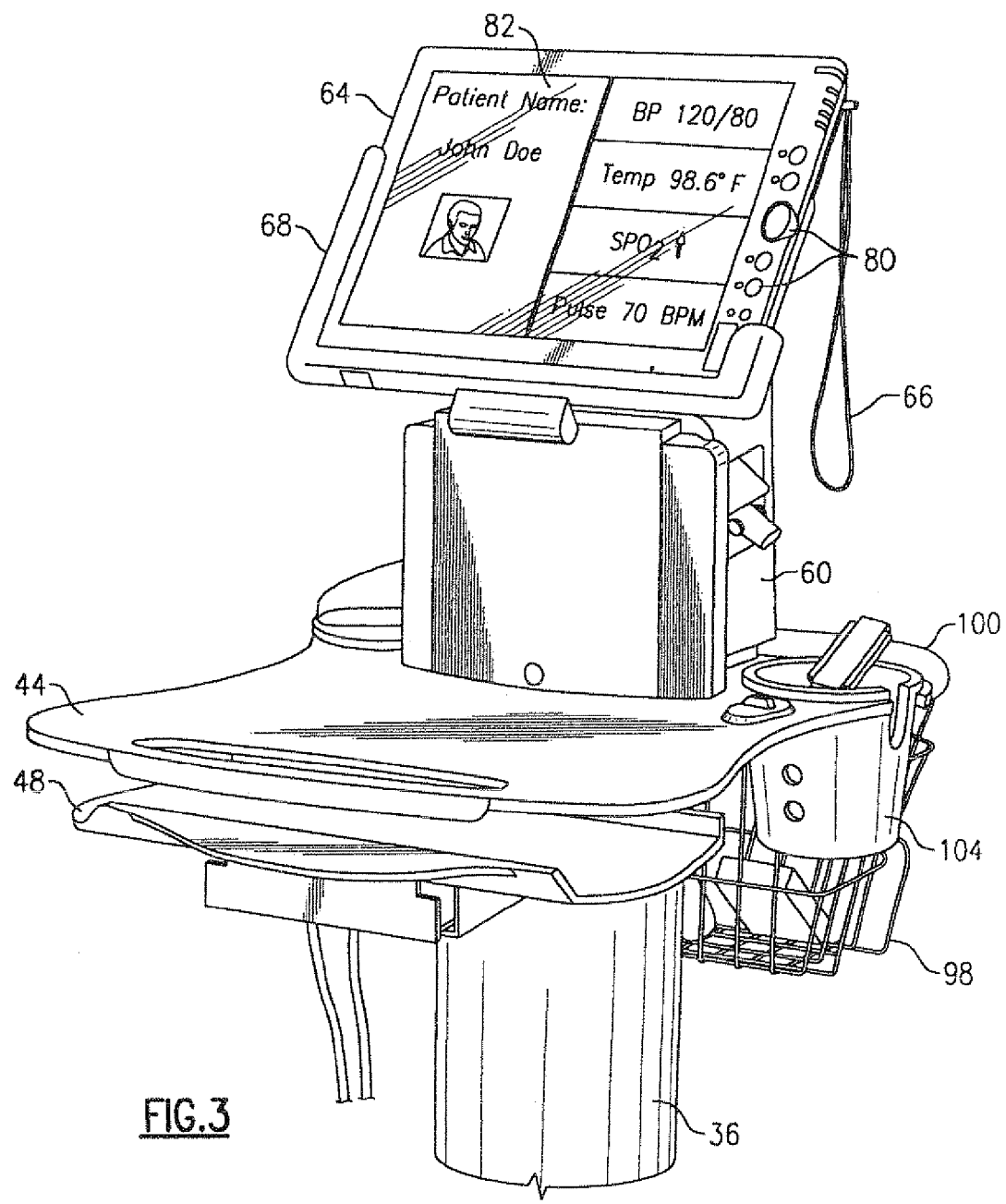
FIG. 3 is a partial front perspective view of the upper portion of the mobile medical workstation of FIGS. 1 and 2.
Figure 4:
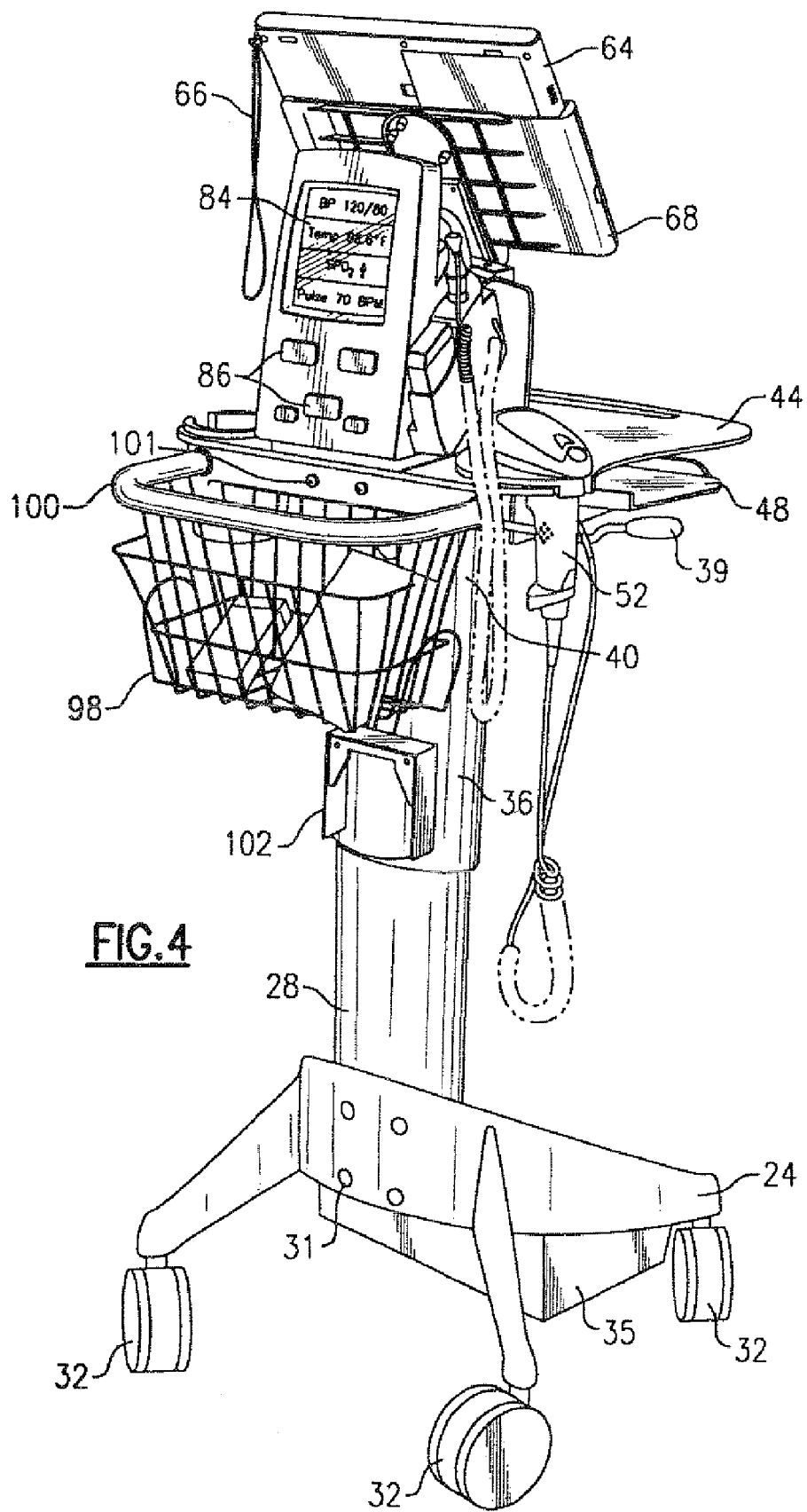
FIG. 4 is a rear perspective view of the mobile medical workstation of FIGS. 1-3.
Figure 5:
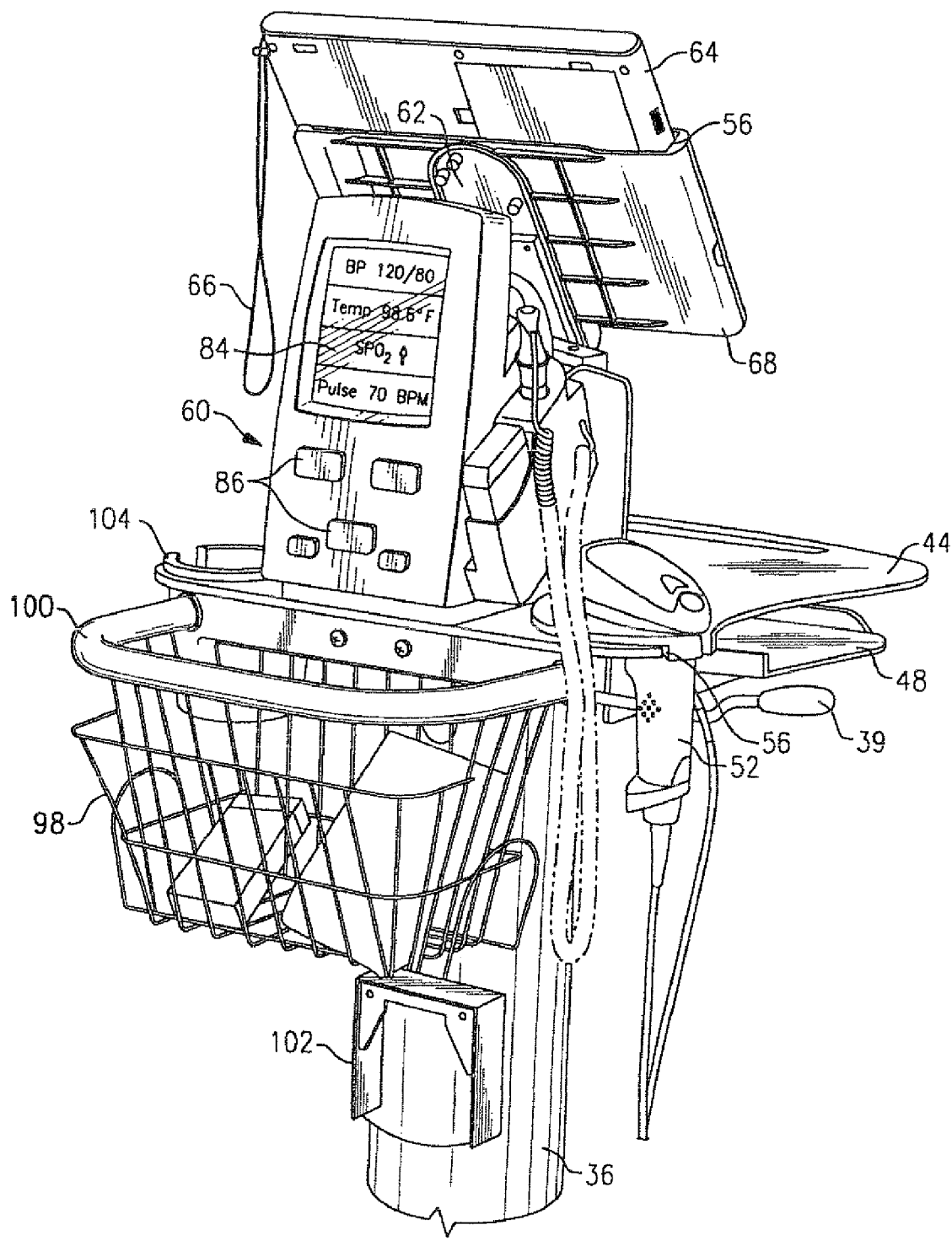
FIG. 5 is an enlarged rear perspective view of the upper portion of the mobile medical workstation of FIGS. 1-4.
Figure 6:
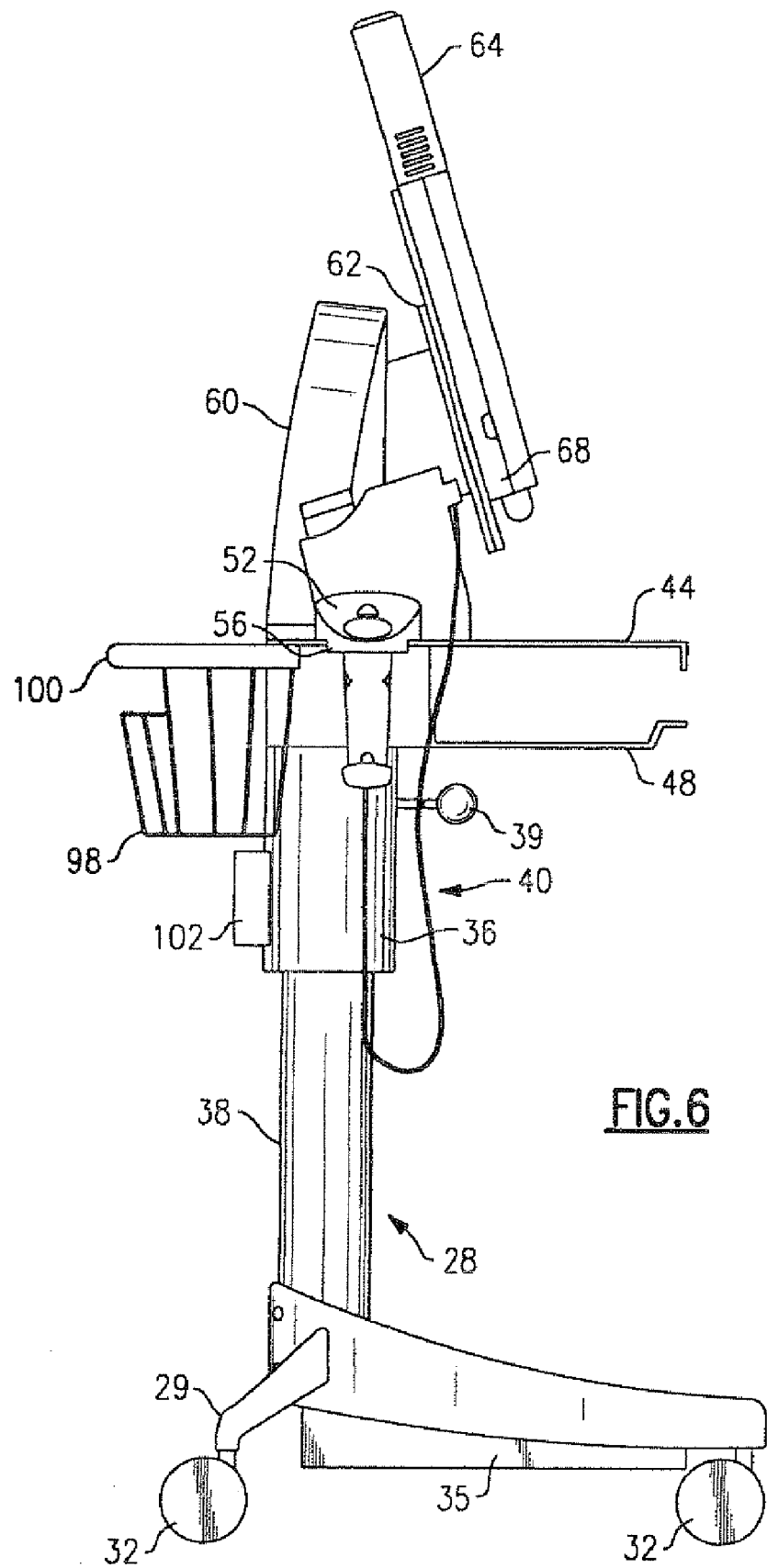
FIG. 6 is a side elevation view of the mobile medical workstation of FIGS. 1-5.

The following description relates to a mobile medical workstation made in accordance with several varied embodiments of the present invention. It should be readily apparent from the following discussion to those of adequate skill that there are numerous configurations that can utilize the inventive concepts related herein. In addition, several terms are used in order to provide a suitable frame of reference with regard to the accompanying drawings. These terms are not intended, unless expressly noted, to be limiting with regard to the intended scope of the invention.

A number of other terms are used throughout the following discussion which bear additional clarification prior to providing a detailed description of the particular embodiments, as follows:

The term "medical instrument" is used to include any device that can be used in conjunction with a patient for purposes of documentation, diagnosis, treatment or therapy during a patient encounter.

The term "computing device" as used herein refers to any form of processing engine, such as a portable laptop computer, personal data assistant (PDA), tablet PC, monitor with a separate hard drive unit, or other similar device. It is intended that this definition should not necessarily limit structure to that having a defined housing. That is, a suitable I/O integrated circuit board linked, for example, to other circuitry and having solid state memory can be conveniently utilized herein for purposes of the invention.

The term "vital signs device", "vital signs collector", and "vital signs measuring device" or "instrument" as used herein refers to any device or apparatus that is capable of collecting one or a varied number of physiologic parameter readings from a patient(s), including but not limited to at least one of blood pressure, ECG, pulse oximetry, body temperature, heart rate, and respiration rate.

The term "supporting structure" refers to any sort of frame or other means capable of receiving, retaining and/or holding a number of discrete components.

The term "wireless" refers to any communication technique which does not require a hardwired connection. Radio frequency protocols such as Bluetooth, WiFi (802.11(b)), Zigbee, frequency hopping, and 802.11(a) and (g) are included in this definition, as well as any other RF, IR, optical or other non-wired communication system.

The term "machine readable" or "machine scannable" refers to information which can be read by a machine. This can include, but is not limited to, one dimensional (1D) and two dimensional (2D) bar code symbologies, as well as optical character recognition (OCR) symbols. The above term can further refer more simply to identification of any other machine perceivable information, such as color or physical parameters, such as sound, light and the like by means of any AIDC (automatic identification and data collection) device. For example, the above definition can further apply to a passive radio frequency (RF) tag that can be used to identify the location of an article or a device using an interrogatory device.

Referring to FIGS. 1-6, the mobile medical workstation 20 according to a first embodiment is a lightweight portable apparatus that includes a wheeled chassis which is defined by a lower base 24 and a supporting structure 28 extending upwardly therefrom. The lower base 24 includes a set of wheels or casters 32 which depend from corresponding legs 29 of the lower base 24 to enable movement of the workstation 20, for example, between patient examination rooms. A foot-actuable pedal 30 is further provided on the lower base 24 to provide braking action and to prevent movement of the mobile medical workstation 20 when the pedal is depressed. A power supply 35, such as a rechargeable battery, is attached to the bottom of the lower base 24. Connections are provided extending through the supporting structure 28 of the workstation 20 to provide an electrical connection to a number of supported components, the components being described in greater detail below, the workstation further having a power cord (not shown) that alternatively permits the workstation to be powered by an AC power supply (not shown) when the battery is uncharged.

The herein described workstation 20 is constructed with a relatively low center of gravity to prevent tipping wherein the lower base 24 is attached to the bottom of the support structure 28 by a set of fasteners 31 according to this embodiment, though alternatively the lower base could be formed integrally therewith or be otherwise attached to the workstation by other suitable means.

The supporting structure 28 of the herein described workstation 20, according to this specific embodiment, comprises an upwardly (vertically) extending main post member 38 which receives the lower base 24 at a lower portion thereof. The supporting structure 28 further includes a translatably (e.g., vertically) movable upper portion 40 defined by a large diameter post member 36 placed in overlaying relation onto the exterior of an upper section of an upwardly extending main post member 38. The upper portion 40 further includes a horizontal work surface 44 as well as a pull-out keyboard tray 48 that are each attached to the large diameter post member 38. Alternatively, the keyboard tray 48 could be attached to a lower surface of the horizontal work surface 44.

The translatably adjustable upper portion 40 of the herein described mobile medical workstation 20 supports a number of items, including a vital signs measuring device 60 and a computing device, in this instance, a tablet PC 64. Each of the devices 60, 64 include an integrated display 84, 82, respectively, each of the devices being attached by suitable means to the top of the horizontal work surface 44. It will be apparent from the following discussion and embodiments that follow that additional or alternative instruments, such as medical diagnostic instruments, can be supported by the workstation 20 wherein attachment of these instruments can be done through several techniques. For example, the vital signs measuring device 60 could be attached via a quick release thumbscrew which is inserted through the post member 36. Other similar techniques, however, can be utilized, such as a set of sliding rails, or other means to effectively retain the device on the workstation 20 which permits releasable attachment thereto.

The vital signs measuring device 60 used in this embodiment is a vital signs monitor such as those, for example, manufactured by Welch Allyn Inc., of Skaneateles Falls, N.Y., or any other instrument that is capable of taking at least one patient physiologic measurement (e.g., blood pressure, pulse rate, respiratory, blood oxygen, body (axillary, rectal, oral, tympanic) temperature, ECG, glucose, among others). The vital signs measuring device 60 according to this embodiment includes a housing to which a plurality of various probes or modules are attached, including an oral thermometer probe, a pulse oximeter probe, and a non-invasive blood pressure (NIBP) module that includes an inflatable cuff or sleeve (not shown). Additional details relating to a particular vital signs device for use with herein described mobile medical workstation, including the above-noted physiologic measuring modules contained thereupon, are provided in copending and commonly assigned U.S. Ser. No. 11/032,625, previously incorporated in its entirety. It will be readily apparent, however, that other vital sign devices such as a Welch Allyn Spot Vital Signs device (Model 53106), a Welch Allyn VSM-300 (Model 53NT0), a Welch Allyn Atlas Monitor (Model 623NP) or a Welch Allyn Propaq Monitor (Model Propaq CS), and in fact other medical diagnostic instruments can be used in lieu of or in addition to those described herein.

Figure 11:
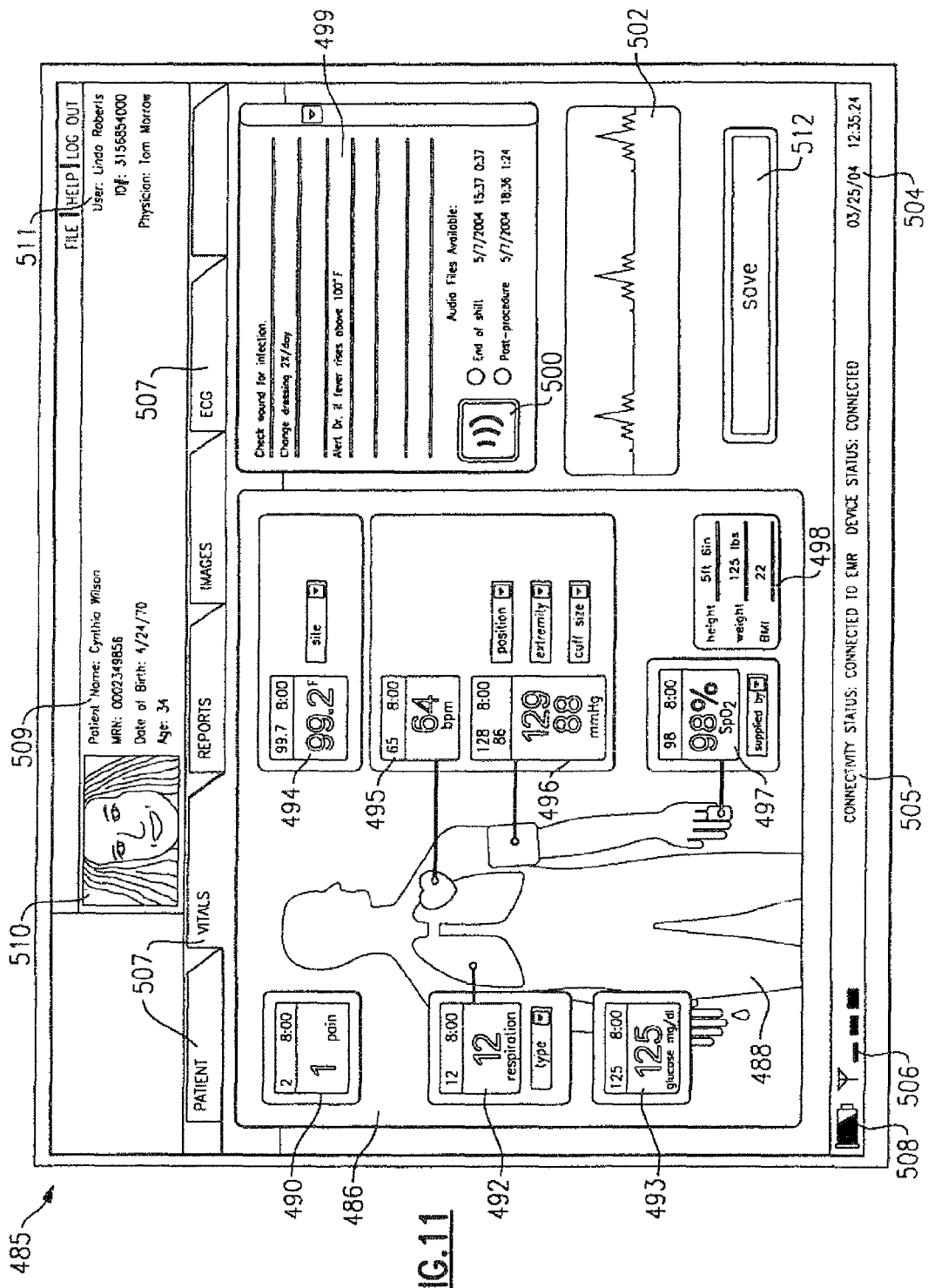
FIG. 11 depicts a graphical user interface of the mobile medical workstation according to one display mode for a monitored patient.

According to this specific embodiment and referring back to FIGS. 1-6, a docking station 68 includes an angled bracket 62 at the top of the upper portion 40 of the supporting structure 28, the docking station further including a contoured recess 76 that is sized for receiving the tablet PC 64 wherein the PC is secured at the bottom and side edges thereof. The tablet PC 64 includes a display 82 and a set of control buttons 80 that are disposed on a user interface. Alternatively, the PC 64 can include a touch screen having a tethered stylus 66, providing a graphical user interface an example of which is shown in FIG. 11, described in greater detail below. It should be noted that the vital signs measuring device 60 or other medical diagnostic instrument used in conjunction with the herein described workstation 20 can also he similarly provided with a docking station (not shown).

The angled bracket 62 enables adjustment of the viewing angle of the tablet PC 64 about a horizontal axis and rotates it to switch between landscape and portrait mode. Preferably, the tablet PC 64 is set a predetermined height above the horizontal work surface 44 wherein the display 82 of the PC 64 and the display 84 of the vital sign measuring device 60 are juxtaposed; that is, the displays face away from each other in opposing directions.

As previously noted, the workstation 20 preferably includes at least one contained battery 35, such as a rechargeable NiMH battery, that is used to power each of the supported devices 64, 60 in lieu of or in addition to their onboard batteries. The workstation 20 also includes a cord (not shown) that permits attachment to an AC power supply (not shown), if needed. Preferably, a single power cord enables recharging of the at least one contained battery 35 and operation during times when the onboard battery power is low. Such power supplies are described in previously incorporated U.S. Ser. No. 10/643,487.

The keyboard tray 48 is disposed substantially beneath the horizontal work surface 44, the tray being deployable from a support to enable a user to pull out a retained keyboard 50 for use, as shown in FIG. 1, the keyboard being used with the tablet PC 64 and interconnected through the docking station 68, although alternatively the keyboard could be a wireless keyboard. As is described in a later portion of this description, the keyboard 50 provides functionality as an input device for the workstation 20, for example, to add manual input concerning a patient to a record. Alternatively, a mouse or trackball could be used as an input device in lieu of or in combination with the keyboard 50, such as shown in the alternate embodiment of FIG. 13A.

The tablet PC 64 and the vital signs measuring device 60 are interconnected according to this embodiment by means of a serial connection, though alternative wired connections, such as USB and wireless connectivity such as Bluetooth or Zigbee could easily be utilized. As will be described in greater detail below, the vital signs measuring device 60 can include a separate microcontroller therein and/or can directly receive input commands via software contained with the tablet PC 64. According to this embodiment, an automatic identification and data collection (AIDC) scanning device, such as a bar code scanner 52, is retained in a lateral slot 56 provided in the horizontal work surface 44. The bar code scanner 52 according to this embodiment preferably includes an imager, such as a CCD, to permit the device to capture images as well as scan and interpret barcodes. According to the herein described embodiment, the bar code scanner is an Image Team 1D (one-dimensional) linear scanner, manufactured by Hand Held Products, Inc., of Skaneateles Falls, N.Y. Details relating to the bar code scanner as an input device for the herein described workstation 20 are briefly described below. Additional details are provided in the previously incorporated U.S. Ser. No. 10/643,387 application.

It should be pointed out that the operational workings and design details of the scanning device do not themselves form an essential part of the present invention in that these details are already acknowledged as being well known. In addition and though a wired barcode scanner is shown for use with the present embodiment, it should be noted that a wireless (e.g., cordless) version thereof would also be suitable, provided any reasonable connection (RF, IR, or other) is made in order to transmit any scanned input to the PC 60. An example of a cordless scanner implementation is depicted in the workstation embodiments of FIGS. 17A and 17B. Each of the above devices 60, 64, 50 and 52 are removable from the herein described workstation 20 for replacement, reconfiguring, or other purposes, as needed, as are any attachments or accessories to the herein described devices.

The supporting structure 28 of the herein described mobile medical workstation 20 further includes at least one storage container in the form of a supporting basket 98 that is attached to the upper portion 40 of the workstation and proximate to the rear edge of the horizontal work surface 44, the basket being sized to permit items such as thermometry probe covers, blood pressure cuffs and other accessories to conveniently be carried. The horizontal work surface 44 of the present embodiment also includes a storage container 104 used for storing a number of device probes, such as a pulse oximetry probe for the vital signs measuring device 64, ECG cabling, and the like. The basket 98 is attached by means of fasteners 101 for attaching to the post 36 and includes a handle 100 permitting the workstation 20 to easily be rolled between patient rooms.

It should be readily apparent that other suitable storage containers and/or carriers can be provided on the supporting structure or otherwise on the workstation. For example, a bracket 102 permitting attachment of at least one other storage container or basket (not shown) is provided on the vertical post member 36. Numerous alternative embodiments of various examples of storage containers and receptacles are further shown, for example, in previously cross referenced U.S. Ser. No. 10/643,387 as well as later embodiments described herein, such as those of FIGS. 17A and 19A. It will be apparent that nearly limitless combinations exist and that merely illustrative examples are provided herein.

As noted, the entire upper portion 40 of the herein described workstation 20 is translatably (e.g., vertically) movable permitting the devices 60, 64, 52, the horizontal working surface 44 and the keyboard 50 to be adjustable as needed, depending on the user and the application. This adjustment further permits each of the displays 82, 84 to be adjusted to enhance viewing by means of a connected lever 39. The lever 39 is connected to an internal gas assist spring (not shown) which is designed to counterbalance the weight of the movable upper portion 40. It should be noted herein that other suitable height adjustment mechanisms, such as those driven by electric motors, could be utilized for selectively adjusting the height of the horizontal work surface 44 and devices 60, 64.

Figure 7:
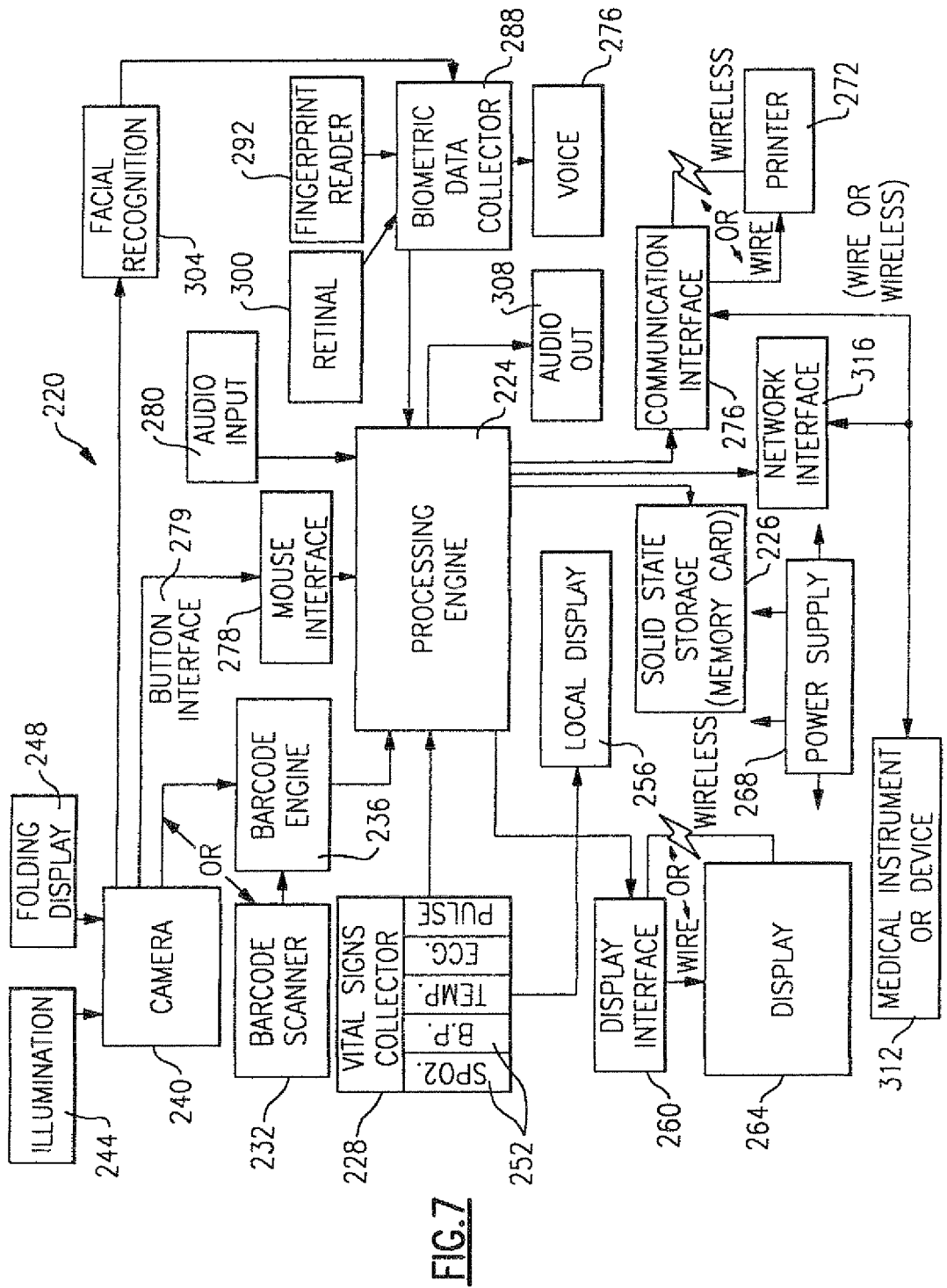
FIG. 7 depicts a functional block diagram for a mobile medical workstation made in accordance with one version of the present invention.

A functional block diagram of a version of the mobile medical workstation 20 is shown in FIG. 7 to aid in understanding the interconnectivity of the supported components of the herein described embodiments. The workstation, identified in this figure as 220, includes a processing engine 224 which for purposes of the present embodiment is included in the tablet PC 64, collectively of the first embodiment. The engine 224 includes memory such as RAM, ROM and a harddrive, shown as 226, to which the remaining functional components are interconnected including a vital signs collector or device 228 and a bar code (or AIDC) seamier 232. The bar code scanner 232 includes a control interface/engine 236 and can further optionally include an integral digital or electronic camera or the workstation 220 can include a separate camera 240 wherein the camera can include an illumination system 244 and optionally, a fold-out or other display 248. The vital signs device 228 includes a number of resident instrument modules 252 such as $S_pO_2$, NIBP, temperature and the like, as well as a local display 256. A display interface 260 and workstation display 264 are also connected to the processing engine 224, wherein the interface can be either a hardwired or a wireless link. In the first embodiment and referring to FIGS. 1-6, the interface between the display of the vital signs device and the computing device 64 is wireless. All of the above are interconnected to a power supply 268, wherein the internal batteries of each of the tablet PC 64 and the vital signs measuring device 60 are not required. Inputs can be made to the processing engine 224 via a mouse interface 278 or through other inputting means, such as a button interface 279, including for example, use of a keyboard 50 of the computing device 64 or the keypad 86 of the vital signs device 60.

Referring back to FIG. 7 with regard to outputs other than those displayed, a printer 272 can also be attached to the processing engine 224 through a separate communication interface 276 which can be hardwired (using USB, for example) or wireless (RF, IrDA, etc) to permit image and/or vital signs readings and other data to be outputted as needed.

According to this system depiction, audio data or input 280 can be added through a microphone or other input means (not shown) to the processing engine 224 which can similarly output any captured audio data via a speaker on the computing device with which audio files can be retrieved, all being shown as 308.

A biometric data collector 288 links to the processing engine 224 whereby specific authorization is guaranteed only through a specific biometric which can include a finger print reader 292, voice signature module 296, retinal scanner 300, or through the use of facial recognition of a user, shown as 300, using the camera 240 or imager of the scanner 232. Other techniques could be included as this diagram is merely indicating examples.

Other medical devices or instruments, represented by 312, can also be interconnected to the workstation 220, including remotely located instruments, which can receive and transmit data over the communication interface 276 such as through a network interface 316, through either a hardwired or wired connection. As such, for example, the workstation 220 can add data concerning a patient(s) from a remote location. In addition, the workstation can further interconnect wirelessly with any patient information system using the network interface. Examples are shown in FIGS. 8 and 22-25.

For purposes of the present invention, the computing capability of the tablet PC 64 can be included separately or redundantly in the vital signs measuring device 60. Communication between the portable vital signs device and a scanner device is also supported wherein the portable vital signs device. Additional details relating to each of the above are provided, in commonly owned and copending U.S. Ser. No. 11/032, 625, previously incorporated herein in its entirety.

According to one embodiment of the flow of communications between one or more portable vital signs devices and a server, in this instance the server being an information server that is operational and that has at least one communication access point that operates according to 802.11b wireless interface protocols. In some settings, such as a hospital, there may be a plurality of 802.11b wireless interface access points connected to the server. A portable vital signs device initiates a communication session by attempting to discover a server access point in us vicinity, and thereby initiate a communication session with the server. In the initial attempt to discover a server, the portable vital signs device transmits a message containing a payload that is understood to be a request to open a session. The server responds to a properly formatted initial message by sending an authorization as the payload of the reply message. The authorization in one embodiment is an authentication message encrypted using a "public key encryption" system, for which the portable vital signs device is provided a decryption algorithm. Each facility can arrange its own encryption and decryption method, for example using at least one 128-bit key that is provided to all portable vital signs devices and all servers of the facility. In addition to the encryption of communications, there is a provision for identifying the authorization type or level of any individual who uses a portable vital signs device, to assure that the requirements of HIPPA are fulfilled. Once a specific portable vital signs device has been provided an authorization by the server, the server sends a message that contains as its payload information enumerating the services that the portable vital signs device can request from the server. Having successfully established bi-directional communications with a server, the portable vital signs device communicates information to, and receives information from, the server. The term information is to be construed broadly, and can include any of data, commands, computer programs or files, and signals related to the good order of the communications, such as signals requesting that the communication pause or resume, that a message or a portion thereof be repeated, that a time signal be provided, or other signals that may be needed to assure proper operation of the system. In some embodiments a plurality of portable vital signs devices can be in communication with the server simultaneously. This means that, in intervals of time perceived by humans as substantially instantaneously, any of portable vital signs devices can send or receive information even though another of portable vital signs devices is also in communication with the server.

In operation, the portable vital signs devices can send information relating to one or more patient encounters, including information identifying the patient, and information relating to the measurements performed and their outcomes. The server can acknowledge the information. When the portable vital signs device receives an acknowledgement that the information it sent has been received and recorded by the server, the portable vital signs device can delete the locally stored information and reclaim the memory space so free for use in another patient encounter.

Diagrams of example interconnection schemes between at least one mobile workstation and a remote hospital server and/or information systems are provided in FIGS. 8 and 22-25, discussed in greater detail below.

With this preceding background being provided of the preferred vital signs device 60 used in the first embodiment, reference is again made of FIGS. 1-6 and 8 wherein the tablet PC 64 is a Wintel computer according to this embodiment; this being any platform preferably consisting of a version of Microsoft Windows running on an Intel 80×86 processor or compatible.

In operation and prior to taking of vitals of a patient, the user 16 would initially log in to the workstation 20 using either the bar code scanner 52, for example, by scanning a user's badge (not shown) or through a password entry via the computing device 64 using the keyboard 50 or using a touch screen (not shown) of the PC using the tethered stylus 66. The display 82 of the tablet PC 64 then indicates whether an existing patient record should be accessed or a new patient record should be created. The bar code scanner 52, according to one version, could be also used wherein a patient's identification bracelet (not shown) or other identification could be swiped or presented thereto wherein the patient identification is matched up with a stored list. If the matchup is successful and results in an existing patient, then the existing patient record can be accessed or alternately, if the patient is not on a matching list, then a new patient record can be created. According to one version, the bar code scanner is an imaging bar code scanner, such as the model Model Image Team 2D scanner that is manufactured by Hand Held Products, Inc. of Skaneateles Falls, N.Y. This imaging bar code scanner includes a housing that includes a handle and an imaging head, the imaging head retaining an illumination system as well as electronic imaging element, such as a CCD, in order to obtain digital images in addition to being able to scan items for machine readable symbologies that can be processed and decoded by the apparatus.

According to this version, the scanner also captures an image of the patient whose vitals are being measured by the workstation. This image is stored into memory and can be displayed during a patient encounter, FIG. 11. Additionally, the scanner can also capture other data in image form, including wounds, rashes, range of motion, and other patient-related data. In addition, the memory of the computing device (or the vitals device) can include a list of authorized users wherein the scanner is used to obtain an image of the user which is compared against stored information before a user can log in to the workstation.

Typical hospitals require the patients to sign a photo release form, even for wound care. The software of the herein described workstation can be used to track these forms and to disable the camera of the scanner if the patient has not yet signed a release. This feature protects the patient's privacy and also provides insulation for liability for the hospital or other medical care facility.

As noted previously, the vital signs device used according to this embodiment can also include a feature for patient identification using an interconnected bar code or other scanning device.

In the instance in which the patient record is new, or in the instance that basic patient demographics need to be added to the record, these demographics can be uploaded from a remote station, such as, for example an Acuity central monitoring station, manufactured by Welch Allyn, Inc., or from a health information system, as shown for example in FIGS. 22-25. Preferably, this transfer can occur through an HL7 or other suitable interface. These patient demographics which are stored into memory can include the patient name, identification number, date of birth, the date the patient checked into the hospital, location, social security number, and gender, among other data. The patient record is then displayed as shown, including the captured patient image and patient demographics, for example, according to that shown in FIGS. 11 and 12 in the display 82 of the supported PC 64 and/or the display 84 of the vital signs measuring device 60. It should be noted that the parameters depicted in the displays 82, 84 according to the Figs. are merely exemplary and can easily be varied.

The user can then by means of the computing device 64 control use or program the vital signs measuring device 60 to either manually or automatically take vitals or other patient readings (e.g., temperature, blood pressure, blood oxygen, glucose, ECG and/or other readings) as needed, once the appropriate sensors of the vital signs measuring device 60 have been attached in a known and accepted manner to the patient. According to an alternative technique, the user can also perform measurements remotely using the bar code scanner 52 which is swiped against an encoded list of menu labels, as described in greater detail in previously cross referenced U.S. Ser. No. 10/643,487.

The workstation 20 permits both automated as well as manual operation of the vital sign measuring device 60 by the user. As such and when the user is operating the vital signs measuring device 60, the user can selectively deactivate the computer display 82, since the user is not using that display which is on the opposite side of the workstation 20. This feature, which can be activated through a button on the user interface 86 of the device 60, addresses privacy and security concerns in the hospital environment. Conversely, the user can control either through the stylus 66 with a touch screen (not shown) or through input via the keyboard 50 or a dedicated hard key thereupon, a similar control to dim or deactivate the display 84 of the vital signs measuring device 60. In fact, the user can totally control the operation via the PC 64 in lieu of the vital signs measuring device 60 to perform measurements. Alternately, and based on similar privacy and security concerns, such as those relating to the Health Insurance and Portability and Accountability Act of 1996 (HIPPA), the user can control the amount of information such that the computer display 82 at the time the user is using the PC 64 may include more information that that of the vital signs measuring device 60 for security and/or privacy concerns.

According to one variation of the invention, the workstation 20 can default to using only the display that the user is working from (the computer 64 or the vital signs device 60) unless a control feature is specifically activated by the user to enable the remaining display (and optionally disabling the remaining display). For example, when the user is performing blood pressure readings and presses the blood pressure measurement button on the console of the vital signs measuring device 60, the processing engine will automatically cause the display 82 of the computing device 64 to dim, since this device is not currently being used. Alternatively, if the user touches the keyboard 50 relating to the computing device 64, then the processing engine will cause the display 84 of the vital signs measuring device 60 to similarly be dimmed. Such dimming of the dormant device can be selected according to this embodiment until the user presses a predetermined button or buttons on either device interface. Alternatively, the user can elect to dim both displays 82, 84 when the workstation 20 is not in use or when the station is in a patient area, for privacy purposes, such as those relating to HIPPA.

Figure 12:
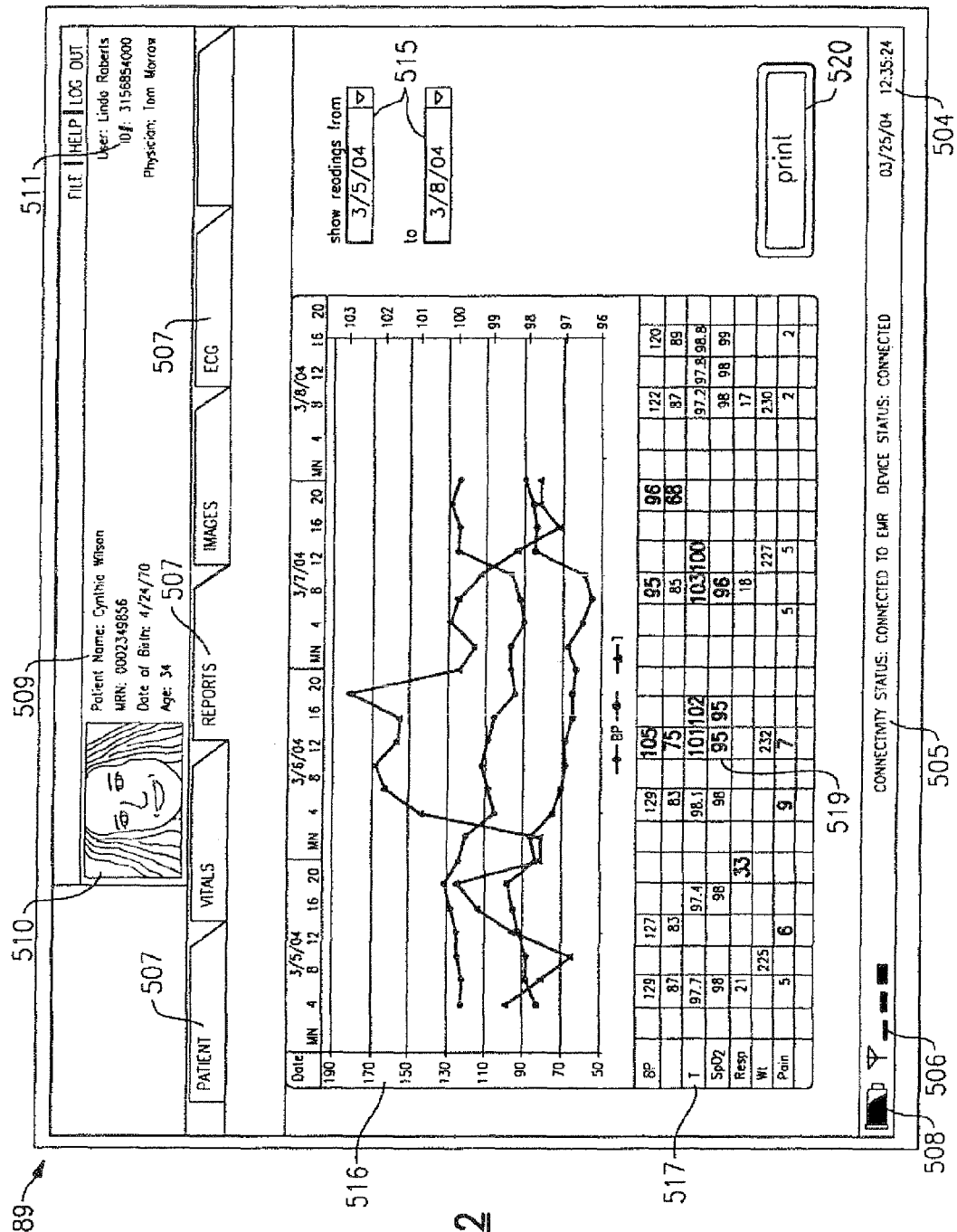
FIG. 12 depicts the graphical user interface of the mobile medical workstation according to another display mode that provides trended patient data.

Sample graphical user interface displays are illustrated in FIGS. 11 and 12 relating to two different display modes of the herein described workstation 20. For purposes of this discussion, the display that is described refers specifically to that of the computing device 64 for ease of explanation.

FIG. 11 represents a graphical user interface for a single patient encounter covering a current situation, wherein the encounter can be recorded using a plurality of display windows. This particular display is obtained by opening one of a plurality of folders 507 provided at the top of the display. For the display mode of FIG. 11, the "Vitals" folder is opened. In a first display window 486, a body representation 488 is provided along with a plurality of data entry boxes that are provided to the user. Several of the data entry boxes 490, 492, 493, 494, 495, 496, and 497 are specifically arranged in relation to portions of the body scale representation 488 to provide a proper guide to the user in the taking of specific physiologic parameters, including pain, respiration, glucose, body temperature, heartrate, blood pressure and pulse oximetry, respectively. An additional data entry box 498 is provided to enter weight and height measurements, as well as body mass index (BMI) which can be calculated by the processing engine of the workstation or the vital signs device. Each of the boxes is labeled, wherein certain of the boxes are shown in relation to representations on the body to assist the user. For example, the pulse oximetry data entry box 497 is disposed in proximity to a depicted finger sensor and the blood pressure data entry box 496 is disposed in relation to an arm cuff depiction on the body representation 488.

The first box 490 representative of pain requires manual entry by the user from a scale of 0-10, in which 0-2 indicates no or little pain and 5-10 indicates higher levels of pain. The second data entry box 492 is representative of respiration rate in breaths/minute, the values also being entered manually along with the type qualifier. Using a touchscreen, the type qualifier can be entered from a menu of choices provided, as discussed below. A third data entry box 493 is representative of glucose, as measured in mg/dL, the value also being manually entered according to this embodiment. On the right hand side of this display window 486 are additional boxes 494, 495, 496, and 497 for entry of body temperature, heart rate, blood pressure, and Sp02, respectively, as automatically or manually obtained by the vital signs device 60. It should be pointed out that patient heart rate can be obtained by either of the temperature, pulse oximeter or blood pressure modules. Typically, one of these modules is preset as the preferred module (e.g., thermometry when axillary). In addition to the readings as communicated from the vital signs device, qualifiers can also be added, such as position or method qualifiers, for example, for blood pressure, the data entry box permits the cuff size (adult, large adult, pediatric) extremity (left arm, right arm, left leg, right leg) and position (lying, sitting, standing) to also be added in addition to the reading, each of the qualifiers being accessed if using a touchscreen using the stylus 66 or through cursor control if using a keyboard 50. As noted, each of the boxes point to representative parts of the represented body display 488 in order to assist the operator. Though the body scale representation is illustrated to provide a suitable means for indicating whether each of the readings has been take, it should be noted that alternative means can be used to indicate the measured values. For example, a blood pressure reading could be represented as they would appear on an actual dial gauge in addition to the measured readings.

As noted, this display window 486 also permits entry of other measurements such as height, weight and body mass index in a separate data entry box 498 using a physical keyboard or using a simulated keypad provided on the touchscreen.

Still referring to FIG. 11, another display window 499 provided on the graphical user interface permits written annotated notes relating to the patient. In addition to the above, the herein described workstation includes means for audio recording, for example, during rounds. As such, notes can be made by a first caregiver pertaining to a particular patient(s) in the instance when a nurse leaving a shift may not have sufficient time in order to speak with the oncoming nurse. According to this embodiment, audio files can be stored with other patient data and can be accessed by a user when the vitals information of the patient is accessed. The audio file can then played back through the user interface on the display. In addition, the user can prioritize audio messages that are left on the workstation, for example, so that the oncoming nurse is aware of the most important issues concerning specific patients first.

The preceding permits notes to be easily captured, for example, in the middle of a procedure such that the nurse or other caregiver does not have to jot the information or message on the back of the patient record, on the back of a paper towel, or even on their hands. As such, capturing this information in the above manner assists the clinician in logging their memory for later documentation. A button 500 is provided to enable recording of a new audio message, the workstation further having at least one indicator (not shown) providing an oncoming nurse or staff member information as to whether any audio files are presently available for playback, the audio files being time and date stamped.

The display further permits other data, such as ECG waveform data, from another instrument connected to the workstation to be displayed in a separate display window 502. The incorporation of an ECG monitoring assembly 576 for use with the workstation is depicted, for example, in FIGS. 13A, 13B, and 14.

The heart rate and the respiration numbers as each appear on the graphical user display are caused to flash, according to one version of the invention, at the same rate as the currently measured rate, even if the measured rate includes irregularities. This form of indication is highly useful in that it easily permits doctors or other users to quickly gauge the status of the patient. For example, a patient with a high heart rate will be indicated with a fast flashing rate. Other parameters, such as respiration rate, could similarly be represented.

In addition, the graphical user interface 485 depicts a time and date stamp 504 as well as providing a connectivity status message 505 with regard to a remote site, such as an EMR, a pictorial depiction 506 of the strength of the radio connection with a remote site through a wireless link, as well as a similar depiction 508 of the state of the battery 35, FIG. 1, of the workstation 20.

In addition to the above, the patient display includes a listing of patient arid user demographics 509, 511 in addition to a captured image 510 of the patient.

Values on the data capture screen that have been already recorded are highlighted; those that still need to be measured are highlighted in a different manner. For example, those that need to still be captured can be shown in gray scale. This will assist a user who is distracted or otherwise interrupted in mid-reading, such as by an emergency, a conversation with the patient or staff member, or other cause.

After all patient information is captured, the user can elect to save the information for storage by the processing engine of the workstation by pressing a save button 512 provided on the interface 485. Alternatively, the saving process can be automated after a predetermined time or when the user switches to a new patient context.

FIG. 12 illustrates a second display mode in which historical patient data can be shown, as reports selected as a folder 507, both tabularly and graphically, for a specific predetermined period of time, selected by the user through menu window 515. A representative set of blood pressure readings are illustrated graphically, shown as 516, with tabular data being provided for each of temperature, blood pressure, Sp02, respiration, weight, and pain, the values being shown as 518.

The display interface 489 further includes a print button 520 that can be accessed to print the trended data. As shown in FIG. 12, values that are outside of a normal range, the range being stored internally, are highlighted, shown as 519. These highlighted values are indicated, whether on the trended data or in the table which readings are being measured, recorded, or automatically measured and recorded.

Figure 14:
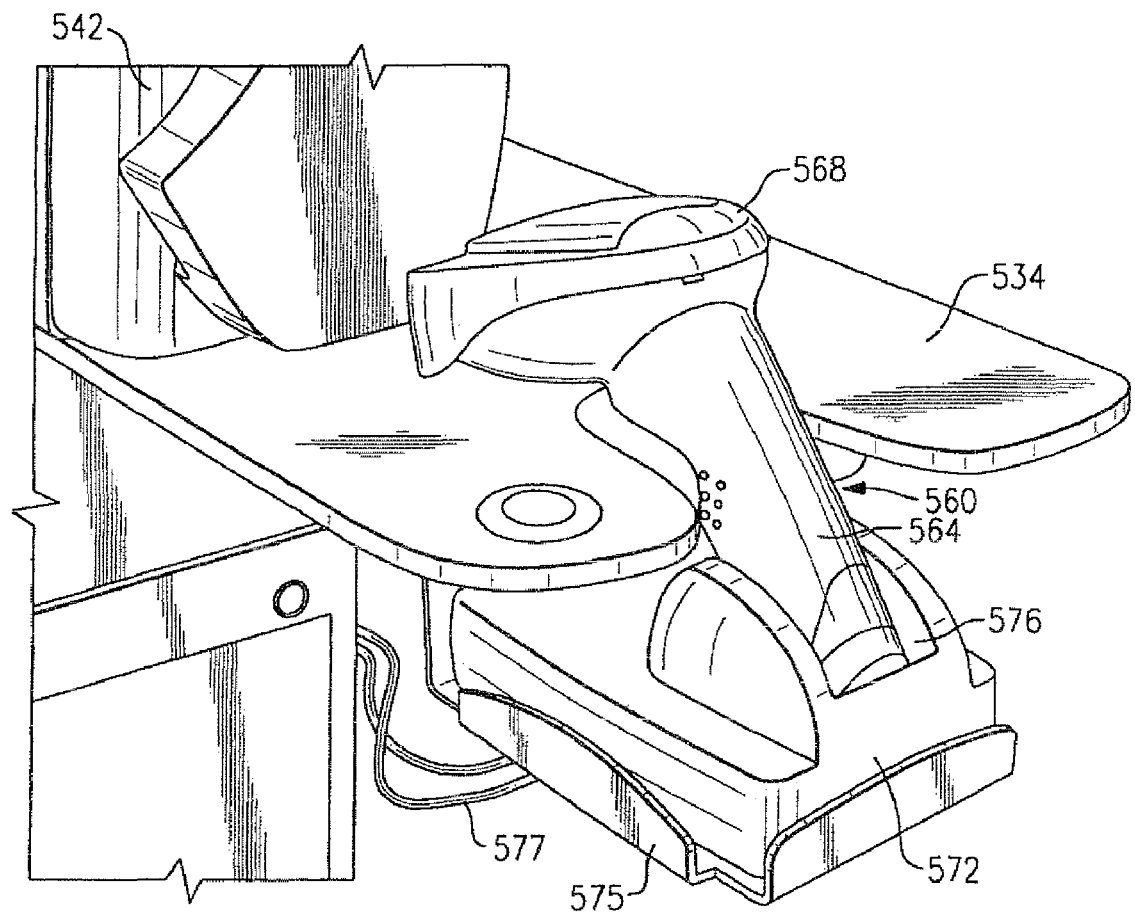
FIG. 14 depicts an enlarged side perspective view of the mobile medical workstation of FIGS. 13A and 13B, showing a presentation scanning device.

Prior to describing additional features, alternative structural embodiments of the herein described workstation are now herein briefly described for the sake of completeness. A second embodiment of a mobile medical workstation in accordance with the present invention is shown in FIGS. 13A, 13B, and 14. In this embodiment, the mobile medical workstation 530 is similarly constructed to the first embodiment in that the workstation is defined by a wheeled chassis having a vertically movable upper portion and a lower base 537 interconnected by a vertically extending post member 539. The upper portion includes a horizontal working surface 534 and supports a number of components including a computing device 538 and a vital signs device 542. The vital signs device 542 according to this embodiment is the identical device used in the preceding embodiment. The computing device 538 is similar in terms of processing capability, but instead includes a monitor 546 that is separately disposed relative to a hard drive 550 that is secured to an upper post member 554.

The workstation 530, according to this embodiment, further includes a bar code scanning device 560. Unlike the preceding embodiment, however, the bar code scanner 560 used in this embodiment is a presentation scanner, such as the Model IMAGETEAM 4620 Cordless 2D Imager made by Hand Held Products, Inc., of Skaneateles Falls, N.Y. As shown most clearly in FIG. 14, the scanner 560 includes a grippable handle 564 as well as an imaging head 568, the scanner being disposed in a slotted portion 576 of a base member 572 set within a tray 575 that is attached to the bottom of the horizontal work surface 534. In the attached position, the imaging head 568 is set at a preferred angled or presentation position relative to the horizontal work surface 534. The scanner 560 is electrically connected according to this embodiment using a USB or other type of connection with the workstation 530 and the processing engine thereof, through cables 577.

In addition, this workstation 530 further includes an ECG monitoring assembly 576, such as a Welch Allyn CardioPerfect PC-based ECG Model CPR-UN-UB-D, which is attached to a USB port (not shown) of the workstation 530 so as to be interconnected with the processing engine of the workstation. According to this embodiment, the ECG monitoring assembly includes a digital ECG module 578 which receives a plurality of lead wires 582, each of the lead wires having an electrode (not shown) attached for placement on the patient in a known manner. The digital ECG module 578 includes a contained processor which converts the analog electrical signals received from the patient into digital values that are transmitted along a transmission cable to the computing device via a serial, USB, or other hardware connection. The processing engine of the workstation 530 is further programmed with a software utility that permits the processed signals to be displayed as waveforms, such as shown in FIG. 12.

Referring to FIGS. 13A, 13B, as well as those workstation embodiments shown in FIGS. 15A and B, 16A and B, and 18A and B, the herein described ECG monitoring assembly 576 is attached to a vertically extending flexible gooseneck 590 that extends from the supporting structure of the workstation 530, enabling the assembly to be stored conveniently for access.

In use, the ECG data can be displayed (e.g., waveforms) as opposed to having to rely solely upon a separate device or a central monitoring station. As such, the herein described workstation permits itself to effectively become an ECG cart, as needed. As in the preceding, the ECG data, like the other vitals data can be stored into memory. That is to say, a predetermined amount of waveform data can be stored for use.

The herein described workstation 530 further includes a keyboard tray 536 which retains a keyboard connected to the computing device. In addition, a mouse 545 is also provided, each being interconnected to the processing engine of the workstation to act as input devices. The workstation 530 also includes baskets 541, 543 for the storage of accessories. The workstation works similarly wherein vitals, including temperature, blood pressure, SpO2, heart rate, and ECG can be captured along with other information in a patient encounter for storage and for transmission of stored vitals to an EMR or other information system.

A third embodiment of a mobile medical workstation 630 in accordance with the present invention is herein described with reference to FIGS. 15A and 15B. This embodiment is nearly identical structurally to that of FIG. 1-6, including a wheeled chassis including a vertically movable upper portion and a lower base 634 that supports a battery 635. The upper portion and the lower base 634 are connected by a supporting structure in the form of a vertically extending post member 639 in which the upper portion includes a horizontal working surface 644. The upper portion supports a computing device 664 and a vital signs device 660, as well as a bar code scanner 560, like that previously described in FIG. 14 and similarly disposed. Storage containers in the form of baskets 616 and 648 are also provided to store accessories and disposables in connection with the supported devices. The workstation further includes a keyboard tray 636 for retaining a keyboard and a mouse 545, each of which are interconnected to the computing device 664.

As previously noted, other vital signs monitoring devices can be used. In this embodiment, the vital signs device 660 is a Welch Allyn VSM-300 Monitor. The workstation further includes an ECG monitoring assembly 576, like that previously described, the assembly including a digital ECG module 578 connected to a set of leadwires 582. As in the preceding, each of the devices 664 and 660 are mounted such that their respective displays are juxtaposed; that is, the displays face opposing directions wherein the processing engine of the workstation permits selective control of each display in order to provide privacy and security to the patient.

A fourth embodiment of a workstation 730 is depicted in FIGS. 16A and 16B. According to this embodiment, the workstation is similar in that it includes a lower base 734 with a contained battery 735, an upper portion that includes a horizontal work surface 744, the upper portion and the lower base being separated by a vertically extending post member 739. The horizontal work surface 744 includes a keyboard tray 768 therebeneath for retaining a keyboard 766 and also includes a mouse 545 which, as in the preceding, is used as an additional input device for a computing device 764 supported on the horizontal work surface. The workstation 730 further includes a pair of storage containers or baskets 716 and 748 disposed on the side and rear facing sides thereof for retaining accessories or disposables, such as temperature probe covers and the like.

The herein described workstation 730 further includes an extending flexible gooseneck 590 which retains the previously described ECG monitoring assembly 576. The workstation 730 further includes a bar code scanner 560, which in this embodiment, is a presentation scanner that is similarly configured to that shown in FIG. 14 relative to the horizontal work surface 744.

In this embodiment, the ECG monitoring assembly 576 is the only dedicated medical diagnostic instrument onboard the workstation 730. In this embodiment, there is no dedicated vital signs device. Alternatively, a container 780 is provided on the rear side of the computing device display for providing storage for supplies needed for ECG (or other) procedures, such as disposable electrodes and skin preparation materials.

A fifth embodiment of a mobile medical workstation 830 made in accordance with the present invention is depicted in FIGS. 17A and B, and 19A-21. The workstation 830 includes a wheeled chassis that includes a lower base 834 and a vertically movable upper portion, as shown more clearly in FIGS. 19A and B. A contained rechargeable battery 835 is retained by the lower base 834, the upper portion and the lower base being separated by a vertically extending post member 839. The upper portion, like the preceding embodiments, includes a horizontal working surface 844 that is used to support a plurality of components, namely a monitor 864 and vital signs monitoring device 860. The supporting structure of the workstation 830 includes a pair of baskets 816 and 848 as well as a laterally extending drawer 884 which retains an ECG monitoring assembly 576, the drawer being located beneath a pull-out keyboard tray 852 that retains a keyboard 854. The workstation 830 further employs a mouse 545 as well as the keyboard as an input device for a computing device, described in greater detail below.

Figure 20:
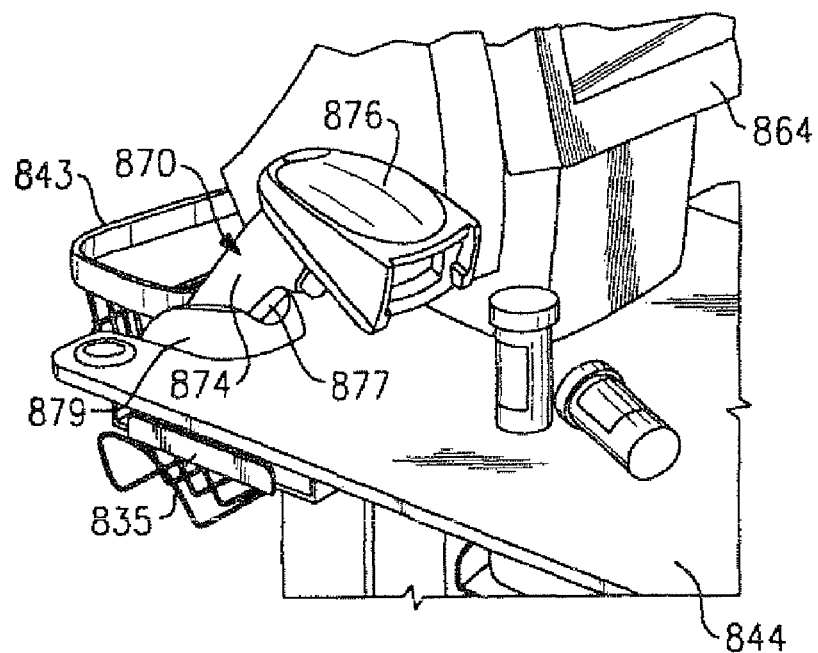
FIG. 20 is a partial side perspective view of the mobile medical workstation depicting a presentation scanning device.
Figure 21:
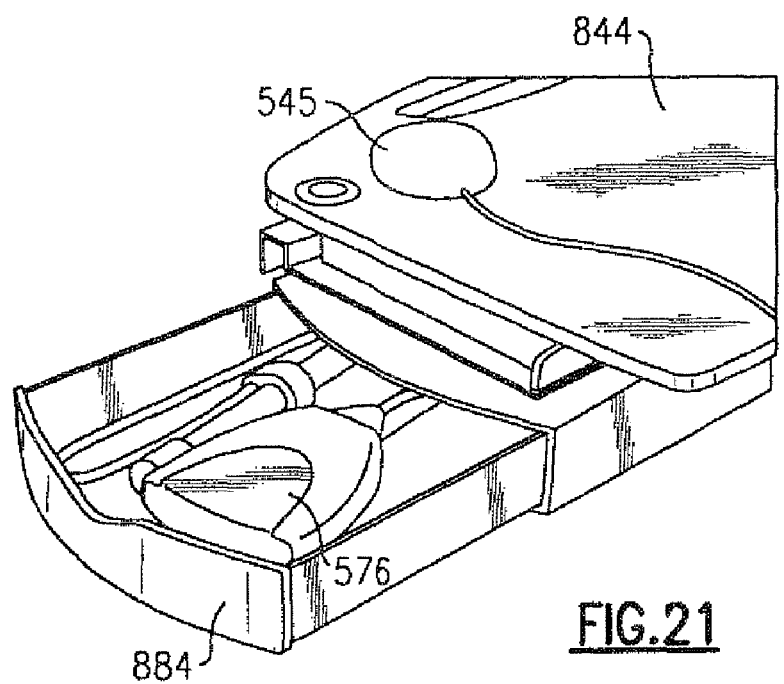
FIG. 21 is an enlarged side perspective view of the mobile medical workstation of FIG. 17A, illustrating an alternative embodiment for storing an ECG monitoring assembly.

The herein workstation 830 includes a bar code scanner 870, which according to this embodiment is cordless and utilizes an access point 880 mounted to the rear of the monitor 864. The display 864 is interconnected to a computing device according to this embodiment that includes a post mounted hard drive 868. As to the presentation scanner according to this embodiment and referring to FIG. 20, the scanner 870 is attached to a rear portion of the horizontal work surface 844, such that the handle 874 is retained within a angled slotted portion 877 of a bracket 879, forming a hands-free stand, the bracket being part of a tray member 885 attached to the bottom of the horizontal work surface 844. In this position, the imaging head 876 of the scanner 870 is aligned angularly with a front facing portion of the work surface. Presentation mode allows the scanner 870 to be left in the hands-free stand and automatically scan for barcodes as objects having barcodes are held in front of the scanner without the user having to manually enable the trigger of the scanner. When the scanner 870 senses an object in its field of view, it automatically illuminates the target and attempts to read the barcode(s).

A sixth embodiment is depicted in FIGS. 18A and 18B. This particular workstation 930 is similar to the preceding in that it includes several of the features thereof. The workstation 930 includes a lower base 934 as well as a vertically movable upper portion. The upper portion includes a horizontal working surface 944 that further includes a keyboard tray 952 and a lateral drawer 984 beneath the tray. The upper portion supports a plurality of components including a display 964, a vital signs measuring device 960 and a bar code scanner 870. An interconnected computing device 968 is attached to an upper post member of the workstation 930. The upper portion of the workstation 930 further includes a vertically extending flexible gooseneck 590, disposed adjacent a rear basket 948 that is used to retain an ECG monitoring assembly 576, as described previously.

Each of the preceding embodiments relate to the system architecture previously described with reference to FIG. 7.

Figure 10:
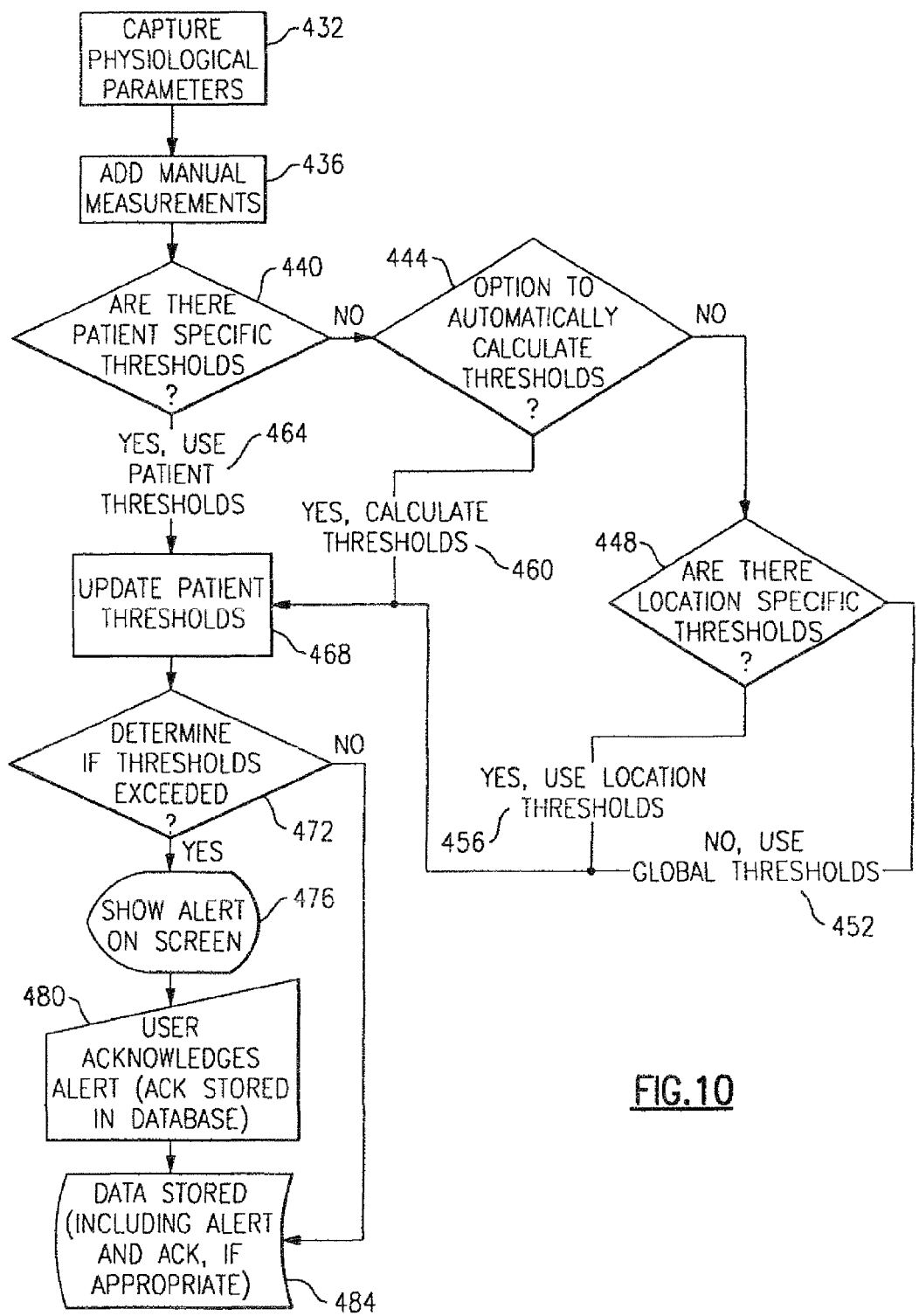
FIG. 10 is a flow chart relating the methodology of the setting of alert thresholds for the mobile medical workstation of the present invention according to one version thereof.

One methodology for how particular thresholds can be set by the herein described workstation is depicted in FIG. 10. First, physiologic parameters (e.g., blood pressure, glucose, pulse oximetry, body temperature, ECG, and the like) are taken and captured as described above, step 432, using the vital signs measuring device and are displayed by the graphical interface. Any manual measurements, such as pain, respiration rate and the like, are also added to complete the patient record for the current timeframe, step 436. Valid ranges for manual vitals measurements according to one version of the workstation are as follows:

| | |
|---|---|
| Systolic Pressures | 60-250 mm Hg |
| Diastolic Pressures | 30-180 mm Hg |
| Inflation Cuff Pressures | 0-300 mm Hg |
| Heart Rates | 10-245 beats per minute |
| Temperatures | 84 F.-108 F. |
| $O_2$ saturation | 40%-100% |
| Mean Arterial Pressure | 40-190 mm Hg |
| Weight Range | 0-600 pounds |
| Glucose | 0-1000 mg/dl |
| Height | 0-120 inches |

In addition, and as previously discussed with regard to the graphical user interface shown in FIG. 11, the workstation permits the use of qualifiers for certain physiologic parameter being measured, whether manual or automatic. Qualifiers provide additional information concerning the conditions of either the patient (standing, lying, sitting on oxygen therapy, etc) and/or the procedure used to obtain the reading. Preferably, all qualifiers are capable of being deleted or modified, though preferably only through a qualified administrator and not a casual user of the workstation. As such, users of the workstation can merely select (or unselect) qualifiers, such as those as follows.

Blood pressure qualifiers, for example, can include location qualifiers such as the left arm, left leg, right arm, or right leg; position qualifiers such as sitting, standing, or lying; method qualifiers such as the cuff size used; and cuff size qualifiers such as adult, large adult, pediatric, small adult, or thigh. Temperature qualifiers can include location qualifiers such as axillary, oral, rectal, or tympanic. Glucose qualifiers can include whether the patient has had a meal and can further include details about the meal. Respiration qualifiers can include method qualifiers such as assisted ventilator, controlled ventilator, or spontaneous; and position qualifiers such as whether the patient is sitting, lying, or standing. Pulse oximetry qualifiers can include oxygen therapy method qualifiers such as aerosol/humidified mask, face tent, mask, nasal cannula, non re-breather, partial re-breather, T-piece, tracheostomy collar, ventilator, venture mask, room air, or oxymizer; and location qualifiers such as ear and finger. Heart rate qualifiers can includes location qualifiers such as whether the radial artery was used, site qualifiers such as whether the rate as determined on the right or left side of the patient; method qualifiers such as whether an auscultatory method was used; and position qualifiers such as whether the patient was lying, sitting, or standing. Weight measuring qualifiers can include quality qualifiers such as whether the weight is actual, estimated, dry, or wet and method qualifiers such as whether the weight was taken with the patient in a chair, standing or in bed. Height qualifiers can include quality qualifiers such as whether the measurement was estimated or actual.

A determination is then made as to whether there are any patient specific thresholds that have been set by the workstation, step 440. For example, the patient may be hypotensive and therefore, the lower threshold for blood pressure may be set to a lower value than for a "normal" patient. This determination is made for all of the captured measurements, including the manually captured readings. If custom thresholds have not been made for the patient, then a determination is made, step 444, for an option to automatically calculate the thresholds. This calculation involves the historical data of the patient for a particular parameter(s). If the option is not implemented, step 448, then a further determination is made according to this embodiment, as to whether there are any location specific thresholds (e.g., whether the patient has had only the left arm measured for blood pressure, whether the patient has been ambulatory, and/or other similar factors).

If the answer to the above inquiry is in the negative, then global (default) thresholds are used by the workstation to create alerts, step 452. In the instances in which there are location specific thresholds, then location thresholds are used, step 456. Similarly, in the instances where the option has been given to automatically calculate patient specific thresholds, then those thresholds are calculated, step 460. These thresholds could be calculated, for example, using historical patient data to estimate an expected range for future patient data (such using the average plus or minus two standard deviations). Other factors could be included, such as clinical risk of estimating either too high or too low, physiological process, and the age of the data (wherein "older" data can be discounted as compared to more recent data). Finally, in the instances in which patient specific thresholds are being used, then the current patient specific thresholds are used 464.

Figure 8:
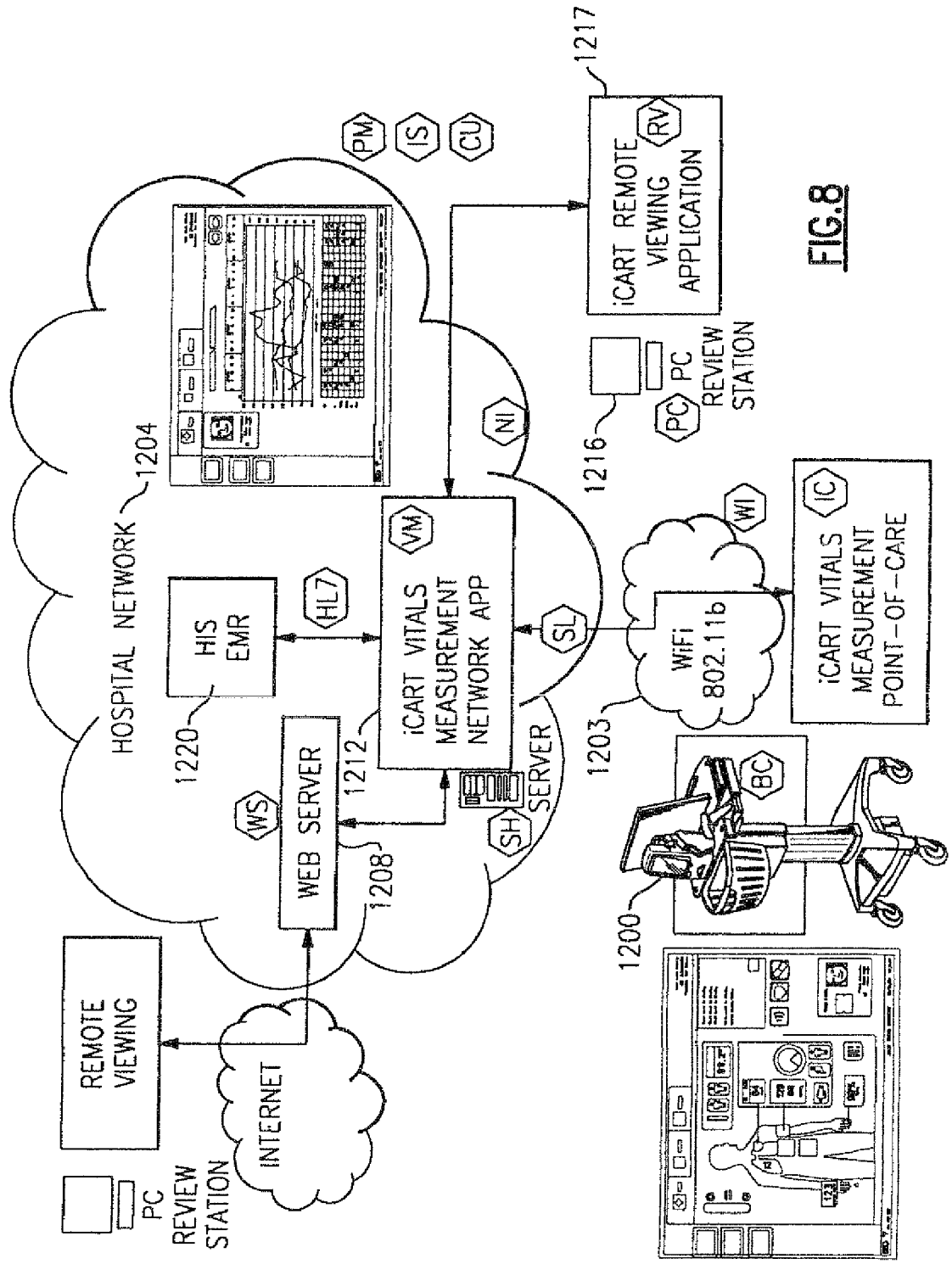
FIG. 8 is a diagrammatic representation of an exemplary communications platform for the mobile workstation defined according to the present invention.

Each of the above thresholds can be updated, step 468, based on current values wherein old thresholds can be replaced with newly derived thresholds. Once the thresholds have either been updated and/or determined for a particular patient, a determination is made as to whether any of the thresholds are exceeded, step 472. If any thresholds have been exceeded, then an alert is shown on either of the displays of the workstation, step 476. This alert can consist, for example, in the form of highlighted numbers, such as shown in FIG. 8, or assume other forms. A user acknowledgement of the alert, step 480, is made on the user interface of either the computing device and/or the vital signs measuring device wherein the acknowledgement of the alert is also stored in the database of the workstation, step 484. The alert can also be transmitted to the central monitoring station or other remote station, depending on the condition of the alert.

Figure 9:
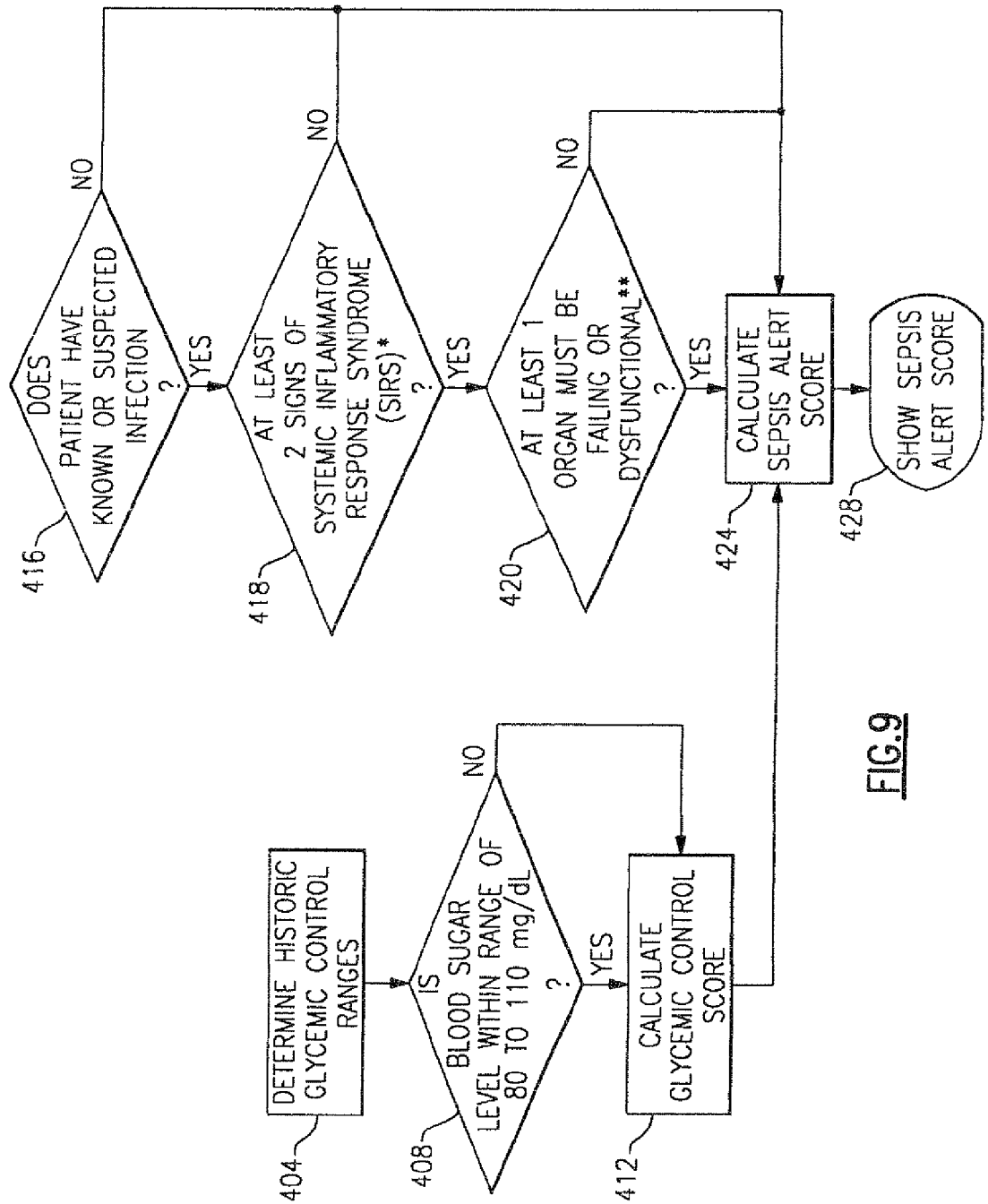
FIG. 9 is a flow chart relating the methodology of a specific alert algorithm for use with the mobile medical workstation, the algorithm relating to severe sepsis.

Referring to FIG. 9, and in addition to providing highlights for out of range values, such as shown in FIG. 12, the processing engine 224 of the herein described workstation can be further programmed according to this embodiment with a number of stored algorithms which are used in order to alert or otherwise apprise the user of significant changes in patient conditions based on changes in certain parameters that are being measured by the workstation and other background information, such as susceptibility to sepsis, stroke, and other conditions. Based on these alerts, users will be notified and given background on the reasons the particular alert was sounded. According to one specific example, illustrated in FIG. 9, the methodology for severe sepsis is illustrated. According to the flow chart shown herein, and according to step 404, a determination is made of the patient's historic glycemic control ranges. This data can be manually input, entered automatically through connected glucometers, or entered through an electronic laboratory system. According to step 408, a decision is made as to whether the blood sugar level of the patient is within the predetermined range of 80 to 110 milligrams (mg)/deciliter (dL). If the patient's blood sugar level is within this predetermined range, then a glycemic control score is calculated, step 412. If the blood sugar level is not within the range, the glycemic control score is also calculated, step 412.

In parallel, a determination is made, step 416, as to whether the patient has a known or suspected infection. If the answer to this determination is in the negative, then the glycemic control score, step 412 is used to calculate a sepsis control score, step 424, which is displayed, step 428. If the answer to the preceding determination is yes, then a followup determination is made, step 418, as to whether the patient has at least two (2) signs of systemic inflammatory syndrome (SIRS). These signs include the following:

a). an elevated heart rate greater than 90 beats/minute;
b). a core body temperature which is either greater than 100.4 F or less than 96.8 F;
c). a respiratory rate greater than 20 breaths/minute; or
  i). PaCO2 which is less than 32 mm/Hg; or
  ii.) Mechanical ventilation for acute respiratory process;
d). a white blood cell count of greater than 12000/mm$^3$ or less than 4000/mm$^3$; or
i). 10 percent immature neutrophils.

If at least two of the above signs are not determined to exist, then step 424 ensues and the sepsis alert score is calculated using the control score determined in step 412. If at least two of the above signs are determined to exist, step 420, then a further determination is made to determine if at least one organ is failing or is dysfunctional. The most common organs that fail are those in the cardiovascular and pulmonary systems. Cardiovascular dysfunction is present if the patient requires a vasodepressor (e.g., norephinephrine or dopamine) to maintain blood pressure, provided that an adequate fluid challenge has been administered. Pulmonary dysfunction is present if a patient requires a fraction of inspired oxygen (FIO2) of 0.50 and has oxygen saturation measured by pulse oximetry values of less than 95 percent, or a PaO2 of less than 100 mm Hg. Patients receiving antibiotics, a vasodepressor, and/or mechanical ventilation consistently meet the criteria for severe sepsis with a high risk for fatality. If the above determination indicates that there is no failing or dysfunctional organ, then step 424 ensues and a sepsis alert score is calculated using the glycemic control score, step 412.

Other examples of patient alerts on the herein described mobile medical workstation using stored readings and other information will be readily apparent to those in the field. For example, a similar alert can be provided when the blood pressure drops below an expected range for a hypertensive or hypertensive patient.

In addition to providing an alert for the user, each clinical parameter which is being measured by the workstation 20 can also be "graded", based on the likelihood of its estimated accuracy. For example, noisy or older blood pressure measurement readings are derated as compared to more current readings. Similarly, manual readings may be given a higher or a lower weighting, for example, depending on whether the manual reading has actually changed. That is to say, a respiration reading that indicates there has been no change may in fact indicate that no reading has been taken at all, as has been known to happen.

The user can be given feedback on the likelihood of getting alerts or false alarms, based on historical data. This will help users set patient specific alerts and help reduce the chance that the alerts will be set too loosely or too tightly. The latter provides guidance for an acceptable range for setting alerts.

According to the present embodiment, the alerts can default to floor level alerts, but the thresholds for the alerts can be moved to more specific values as more is learned about the patient and expected and typical variations in parameter readings.

According to another version, the present medical mobile workstation is equipped to inform the use of the correct inflation cuff or sleeve size for use in measuring blood pressure, since readings can be inaccurate with the wrong cuff size (e.g., use of a pediatric cuff on an adult). The cuff size can be determined by measuring the amount of air being pumped into the cuff at the time of inflation.

Alternatively, the scanning device 52, FIG. 1. can be used in conjunction with the workstation to read a machine scannable label (not shown) located on the inflatable cuff (not shown) itself, which the user can scan using the device prior to taking a measurement in order to document the size of the cuff that is being used. The cuff can be read by either removing the scanner from the workstation or alternately using the presentation mode, as shown in the embodiment of FIG. 18.

According to one version of the invention, the software provided in the workstation (e.g., either in the computing device and/or in the vital signs device) can be programmed such that the user must first scan the machine readable label using the scanning device 52, FIG. 1, each time a blood pressure measurement is to be taken. Alternatively, the scanning of the label could take place after the cuff has been secured to the patient wherein the scanning of the label itself initiates the inflation of the cuff and the measurement of the patient. According to the preceding, the scanning step herein described can be used to accomplish multiple tasks; that is, to document the cuff being used and identify the cuff size, as well as to initiate the measurement by starting the inflation pump.

In the presentation mode, the scanner can effectively scan any item placed on the horizontal work surface, such as prescription bottles, patient records (not shown), and the like. The scanner can also be removed as needed from the socket wherein the scanner can either be attached to the computing device of the workstation by means of a wired connection or alternatively through an RF or other wireless (e.g., cordless) connection.

The use of the herein referred to scanner permits an additional feature with regard to the herein described mobile medical workstation. This feature relates to the measurement of a patient's fluid balance though the relative measurements of intakes and outputs. According to previously known methods, measurement of a patient's fluid balance has required manual, imprecise methods, such as the gauging of the amount of fluid contained in a urine bag or alternately, the amount of fluid remaining in a cup of water. The nurse or clinician would be pressed to perform arithmetic operations based on the above gauged measurements resulting in a labor intensive and often error prone process.

According to a version of the present invention, each fluid container used by a patient can include a series of bar-code or other machine codable labels. These labels are predisposed at specified locations, preferably along the exterior of the container, so as to indicate a predetermined amount of fluid. In use, the user would scan the bar code label at the location of the container closest to that of the resulting fluid level. Among the encoded information contained on the label would be the type of liquid (e.g., water, urine, etc) within the container, as well as the volume of fluid in the container based on the location thereof.

In operation, the user scans a container label, which is then decoded by the scanner, and the processed results are stored within the microprocessor of the workstation and or selectively displayed on either the display of the computing device and or the display of the vital signs measuring device. Upon repeated readings, depending on whether the fluid indicates inputs or outputs, the workstation is further programmed to update previous results and store current results. A tabular or other listing of all fluids for a predetermined period can also be accessed from memory for display, if required, wherein the results can also be transmitted along the wireless link to the EMR or other remote station, as needed.

In addition to the preceding as to determination of the cuff size, the herein described workstation 20 can further be programmed to more efficiently and reliably take blood pressure readings based on the already known history of a patient(s). According to this version of the invention, the microprocessor of either the computing device and/or the vital signs measuring device can effectively record a trended history of the patient, including the patient's blood pressure readings, such as shown according to FIG. 8. A patient specific history can be developed using these measurements wherein it can be ascertained whether a patient is hypotensive (i.e., having low blood pressure) or hypertensive (i.e., having high blood pressure).

By reference to the already existing record of patient readings, such as those shown in FIG. 12, the workstation 20 can be programmed such that the blood pressure measuring module can be set to inflate an attached cuff to a predetermined inflation pressure, as based on the historical data of the patient. For example, if a patient is hypotensive and has not had a systolic blood pressure reading that has exceed 100 mm Hg, then the workstation 20 can be programmed such that the patient will not have his or her cuff inflated above 120 mm Hg, instead of the normal 160 mm Hg that the blood pressure module is typically set (the default pump setting). According to this embodiment, a sufficient or predetermined number of readings within a specified time period would first have been accumulated prior to implementing any customized inflation pressure setting.

Alternatively and for hypertensive patients, the blood pressure module can be programmed by instructions stored in either the computing device and/or the vital signs measuring device, also based on historical data, to inflate the attached cuff to a predetermined inflation pressure that is greater than the default pump setting in order to obtain a more reliable measurement, with the measurement being made in a shorter amount of time. The latter technique would avoid having to inflate the cuff at the default setting, not be able to obtain a suitable reading based on the blood pressure reading history of the patient, and having to reinflate the cuff a second time to a higher pressure in order to obtain an accurate blood pressure reading. As should be apparent, the preceding operation is less intrusive to the patient and is much more efficient.

In addition to the above, the herein described blood pressure module can be also be selectively programmed to operate as a tourniquet in order to perform venipuncture, in addition to performing blood pressure measurements. According to one version, the inflatable cuff, when attached to the patient prior to phlebotomy, can be used to measure blood pressure in the above described manner. Immediately following this measurement, the module, as programmed by the computing device, reinflates the cuff to a precise pressure (e.g., preferably to that pressure where the pressure vacillates due to heart pressure pulse). At this pressure, the cuff permits the nearby blood vessels to distend, making these vessels much easier to detect and to puncture, such as for the taking of blood samples. The cuff automatically deflates after a predetermined period of time, for patient safety, or alternatively the procedure can be stopped manually at the user interface.

The herein described workstation provides a mobile communications portal for the hospital environment setting. According to one version, the workstation includes a speakerphone or a headset that enables the user to make or place VOIP (Voice on Internet Protocol) calls directly from the patient's bedside.

In addition, the computing device of the workstation permits email access by way of the above described Internet connection wherein the user can further access, for example, the message system of an EMR, a consulting physician, or other contact, as needed. To handle HIPAA concerns, the e-mail can have any reference to patient demographics removed and instead provide the physician with a web link (requiring a password) to view the data.

Additionally, users can selectively or automatically page clinicians and staff through the PC-based system at the patient's bedside. For example, the user can selectively page housekeeping when a room needs to be cleaned, or the workstation can be configured to automatically page the nurse's station when anomalous readings are confirmed, or the pharmacy can be similarly paged in order to obtain a prescription. Varied other uses can be imagined, as the preceding list is merely one example.

Referring now to FIGS. 8 and 22-25, additional discussion is made concerning the potential connectivity of the herein described workstation in a hospital or physician office environment.

Referring first to FIG. 8, there is depicted a pictorial representation of a mobile workstation 1200, as previously described herein, linked to a hospital network 1204 by way of a WiFi (802.11(b)) bi-directional wireless connection 1203 wherein the network includes a web server 1208 configured with a measurement database network application 1212 that synchronizes data from the workstation and permits communication with other remote stations, such as remote PC stations 1216 equipped with software 1217 to allow viewing and editing of data obtained over the network. The network application software 1212 further permits interconnection to a Health Information System (HIS) or Electronic Medical Record (EMR) database 1220 wherein vital trending and archiving can be performed. In addition, the software application 1212 permits notification of abnormal readings while the web server permits remote access of data by review stations 1224 over the Internet.

Figure 22:
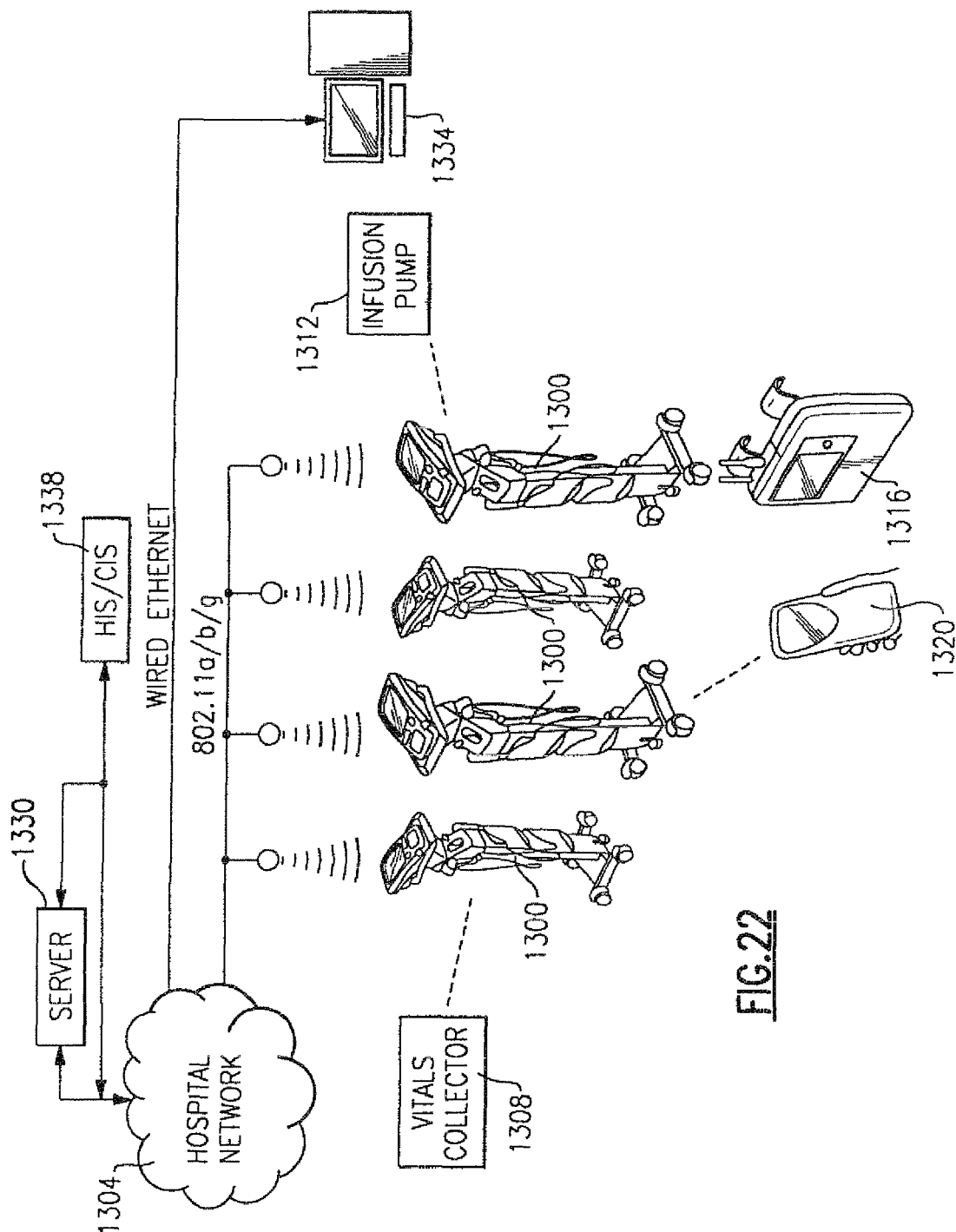
FIG. 22 is a pictorial representation, partially diagrammatic, illustrating a mobile medical workstation in accordance with the present invention as used in clinical environment.

Additional examples of remote interconnection schemes are depicted in FIGS. 22-25, these examples being described in greater detail in U.S. Ser. No. 10/643,487, previously incorporated above in its entirety. For example, FIG. 22 represents, by way of example, a plurality of workstations 1300 in connectivity with a plurality of physiological parameter measuring instruments and a hospital network 1304.

Still referring to FIG. 22, the workstation(s) 1300 can be placed into wireless communication linkage using Bluetooth, WiFi (802.11(b)) or other wireless protocol with other components, and particularly with other devices found in the patient room, for example a vital signs collector 1308, such as the Spot vital signs collector manufactured by Welch Allyn, Inc., and an infusion pump 1312, such as, for example those manufactured by Abbott Laboratories, Inc. As previously noted, the specific details of any of the above noted wireless communications protocol are known in the field and of themselves are not considered part of the invention. Similar connections can also be made between the workstation 1300 and other portable devices 1316, 1320, such as other vital sign monitors such as the Welch Allyn Propaq and Welch Allyn Micropaq monitors, for example.

The workstations 1300 in this example are further configured into a computer network 1326 wherein data from the workstations is transmitted by means of a 802.11a/b/g protocol using a workstation server 1330 that is further linked by an Ethernet connection to a remote computer review station 1334 and a Computer Information System or Health Information System (CIS/HIS) 1338, such as an Electronic Medical Record (EMR) system. In operation, the wireless connection between the instruments 1308, 1312 and the workstation 1300 permits patient data to be acquired using the contained scanning device or keyboard controls, or alternately a specific control button on the console of the workstation 1300. As to the wireless control of each of the infusion pump 1312 and the vital signs collector 1308, the communications linkage with the workstation(s) 1300 enables control of each so as to provide a virtual control interface at the workstation 1300. Readings are taken, in the case of the vital signs collector 1308 and are transmitted to the workstation 1300. The readings are stored into memory of the computing device on board the workstation 1300 and can then be uploaded onto the hospital network 1304, either automatically when the workstation 1300 passes an appropriate wireless access point (not shown) in the hospital, or selectively by way of a control button or by keyboard control enabling same on the workstation, for example.

Figure 23:
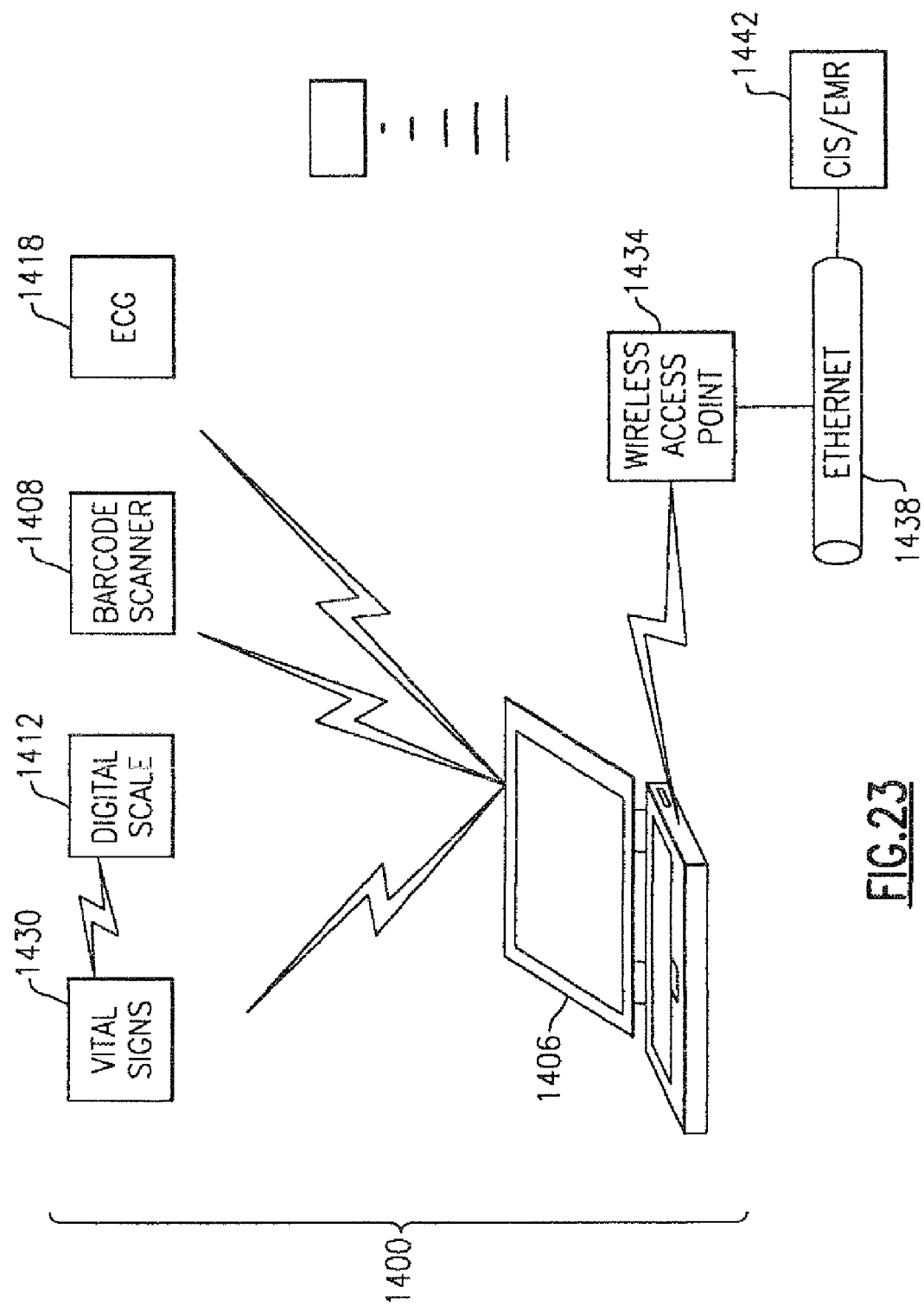
FIGS. 23-25 represent diagrams of single and multiple configurations involving the mobile medical workstation in accordance with the present invention.
Figure 24:
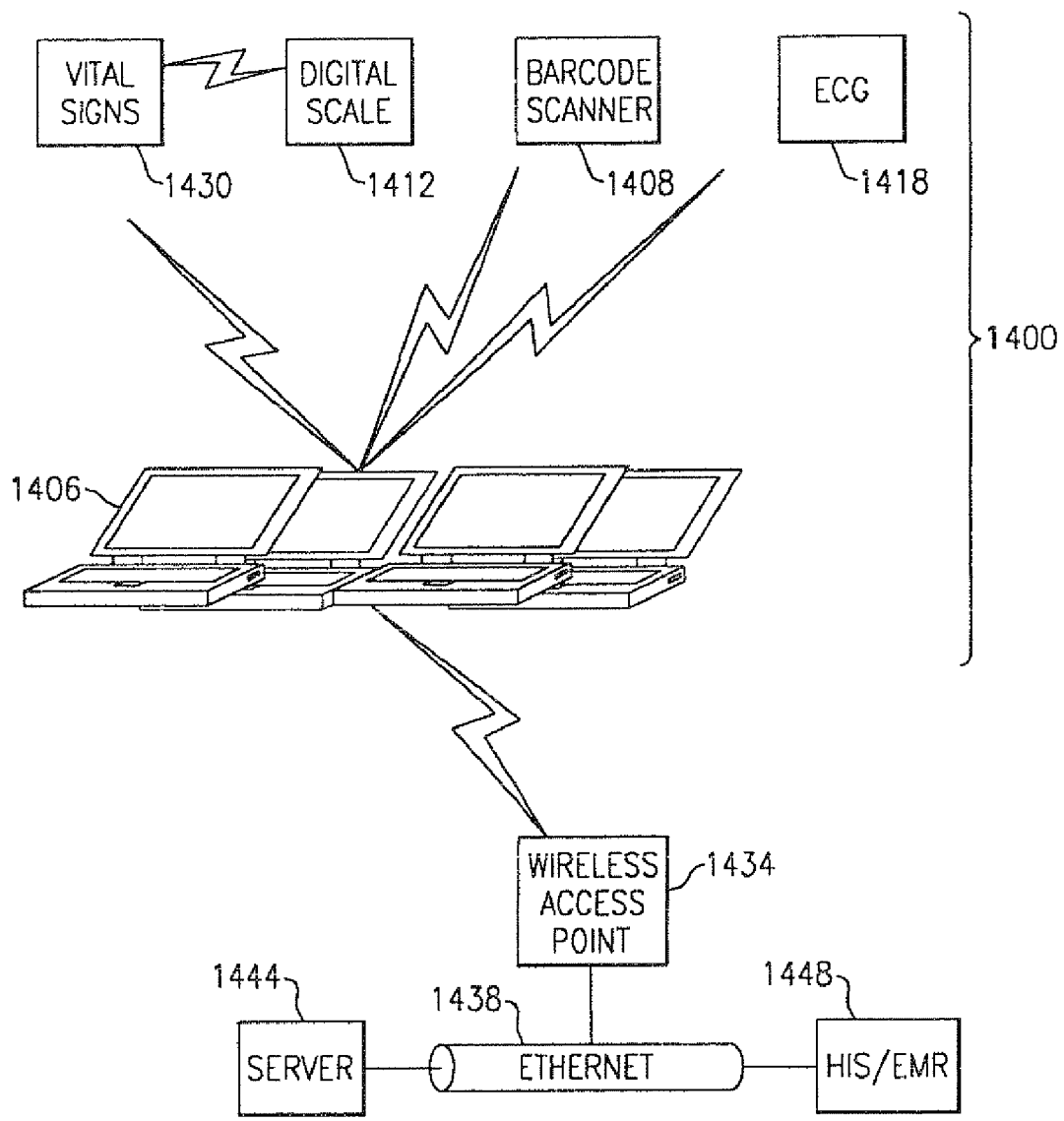
Figure 25:
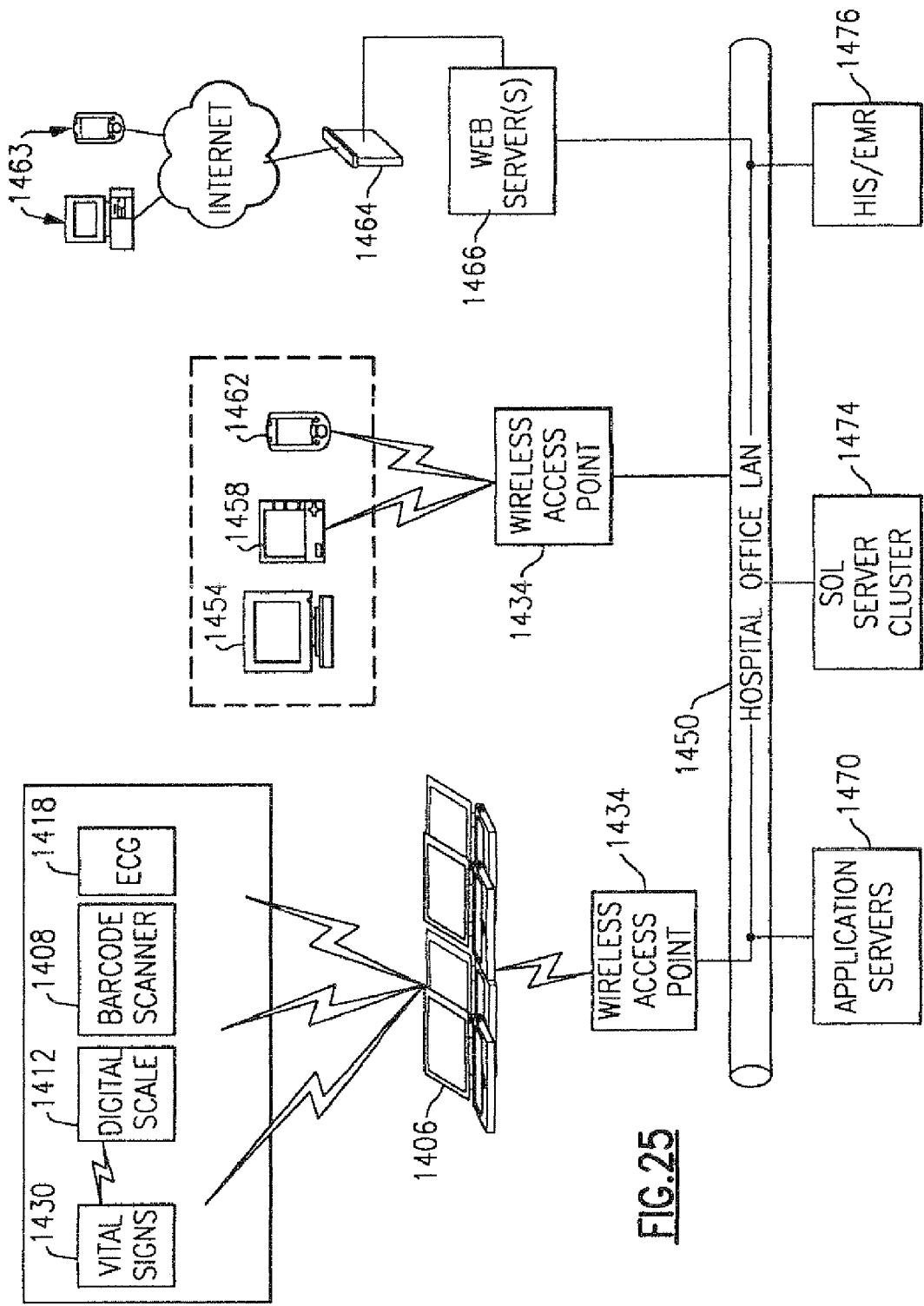

Referring to FIGS. 23-25, there are shown other alternative embodiments for network connections involving the herein described mobile medical workstation. For purposes of these embodiments, by way of example, certain specific integrated instruments have been selected for use with the workstation, shown herein as 1400. In FIG. 23, a single workstation 1400 is shown only diagrammatically. According to this embodiment, the workstation 1400 includes an integrated bar code scanner 1408, a digital scale 1412, such as those manufactured by Tanita, mc, and an ECG assembly 1418, such as Welch Allyn's Cardio Control Module, each of the foregoing components being hard wired in this example, such as through a USB or other suitable connection, to the computing device within the supporting structure (not shown) of the workstation 1400. A vital signs collector 1430 is wirelessly connected via Bluetooth or other suitable protocol thereto. In this embodiment as shown, the digital scale data is collected by the vital signs collector 1430, with both sets of data being transmitted wirelessly to the workstation 1400. Alternately, the digital scale 1412 could communicate directly with the workstation 1400.

The workstation 1400, being mobile, is capable of uploading information when it passes an appropriate wireless access point 1434 through connection with a hospital network, as previously noted, using an 802.11(b) or other suitable protocol in which the data can be transmitted to an CIS/EMR system 1442 through an Ethernet connection 1438.

Referring to FIG. 24, a small plurality of workstations 1400 (approximately 3-10 workstations) are shown for connection, each of the workstations also similarly including the wired connections with the scanning device, ECG monitoring assembly 1418 and the digital scale 1412 with the computing device 1406 of the workstation 1400. Only one each of the above devices is shown for clarity purposes. The computing devices 1406 are linked through an access point 1434 (only one of which is shown) in the hospital setting to a server 1444 and a Health Information System/Electronic Medical Record (HIS/EMR) system 1448, the latter being suitably linked through a wired Ethernet connection 1438.

Referring to FIG. 25, a larger plurality (greater than 20) of workstations 1400 are depicted for use in a hospital/office local area network (LAN) 1450 in which the computing devices 1406 are linked wirelessly thereto by means of wireless access points 1434. The network 1450 further includes an interconnection whereby data from the workstation 1400 can be uploaded to one of a computer workstation 1454, a tablet PC 1458, and/or a pocket PC 1462, each of these components also being wirelessly linked to the network 1450 by means of an 802.11 protocol. The network 1450 also provides a remote Internet connection through a firewall 1464 to a number of similar devices 1463, the data being managed by an appropriate web server 1466.

The network 1450 also includes multiple servers in the form of application servers 1470, an SQL (Structured Query Language) Server Cluster 1474, and an HIS/EMR System 1476, which allow for remote viewing and analysis of data collected by the workstation 1400. It should be readily apparent that other variations are possible within the intended scope of the present invention.

| PARTS LIST FOR FIGS. 1-25 | |
|---|---|
| 16 | user |
| 20 | mobile medical workstation |
| 24 | lower base |
| 28 | support structure |
| 29 | legs |
| 30 | brake lever |
| 31 | fasteners |
| 32 | wheels (casters) |
| 35 | battery |
| 36 | larger diameter post member |
| 38 | main post member |
| 39 | lever |
| 40 | upper portion |
| 44 | horizontal work surface |
| 48 | keyboard tray |
| 50 | keyboard |
| 52 | bar code scanner |
| 56 | slot |
| 60 | vital signs measuring device |
| 62 | angled bracket |
| 64 | tablet PC |
| 66 | stylus |
| 68 | docking station |
| 76 | conformed recess |

| -continued | |
|---|---|
| PARTS LIST FOR FIGS. 1-25 | |
| 80 | controls |
| 82 | display |
| 84 | display |
| 86 | user interface |
| 94 | thermometry unit |
| 98 | basket |
| 100 | handle |
| 101 | fasteners |
| 102 | bracket |
| 104 | storage container |
| 220 | workstation |
| 224 | processing engine |
| 228 | vital signs collector |
| 232 | barcode scanner |
| 236 | barcode control interface |
| 240 | camera |
| 244 | illumination system |
| 248 | folding display |
| 252 | instrument modules |
| 256 | local display |
| 260 | display interface |
| 264 | display |
| 268 | power supply |
| 272 | printer |
| 276 | communication interface |
| 278 | mouse interface (keyboard) |
| 279 | button interface |
| 280 | audio input |
| 288 | biometric data collector |
| 292 | fingerprint reader |
| 296 | voice encryption module |
| 300 | retinal scanner |
| 304 | facial recognition |
| 308 | audio output |
| 312 | medical instrument or device |
| 316 | network interface |
| 404 | step |
| 408 | step |
| 412 | step |
| 416 | step |
| 420 | step |
| 424 | step |
| 428 | step |
| 432 | step |
| 436 | step |
| 440 | step |
| 444 | step |
| 448 | step |
| 452 | step |
| 456 | step |
| 460 | step |
| 464 | step |
| 468 | step |
| 472 | step |
| 476 | step |
| 480 | step |
| 484 | step |
| 485 | graphical user interface |
| 486 | display window |
| 488 | body scale representation |
| 489 | display interface |
| 490 | data entry box |
| 492 | data entry box |
| 493 | data entry box |
| 494 | data entry box |
| 495 | data entry box |
| 496 | data entry box |
| 497 | data entry box |
| 498 | data entry box |
| 499 | display window - annotation |
| 500 | indicator - audio note |
| 502 | ECG display window |
| 504 | time/date stamp |
| 505 | connectivity status |
| 506 | radio signal strength indicator |
| 507 | folders |
| 508 | power indicator |
| 509 | patient demographics |

-continued

PARTS LIST FOR FIGS. 1-25

| | |
|---|---|
| 511 | user demographics |
| 512 | "save" button |
| 515 | date range of readings |
| 516 | graphical trend data |
| 517 | tabular trend data |
| 519 | highlighted values |
| 520 | "Print" button |
| 530 | mobile medical workstation |
| 534 | horizontal work surface |
| 535 | battery |
| 536 | keyboard tray |
| 537 | lower base |
| 538 | computing device |
| 539 | vertically extending post member |
| 541 | basket |
| 542 | vital signs device |
| 543 | basket |
| 545 | mouse |
| 546 | monitor |
| 550 | hard drive |
| 554 | post member |
| 560 | barcode scanner |
| 564 | grippable handle |
| 568 | imaging head |
| 572 | base member |
| 576 | slotted area |
| 578 | digital ECG module |
| 590 | gooseneck |
| 616 | basket |
| 630 | mobile medical workstation |
| 634 | lower base |
| 635 | battery |
| 636 | keyboard tray |
| 639 | vertical extending post member |
| 644 | horizontal work surface |
| 648 | basket |
| 660 | vital signs device |
| 664 | computing device |
| 716 | basket |
| 730 | mobile medical workstation |
| 734 | lower base |
| 735 | battery |
| 739 | vertically extending post member |
| 744 | horizontal work surface |
| 748 | basket |
| 764 | computing device |
| 766 | keyboard |
| 768 | keyboard tray |
| 816 | basket |
| 830 | mobile medical workstation |
| 834 | lower base |
| 835 | battery |
| 839 | vertically extending post member |
| 844 | horizontal work surface |
| 848 | basket |
| 852 | keyboard tray |
| 854 | keyboard |
| 864 | monitor |
| 868 | hard drive |
| 870 | bar code scanner |
| 880 | access point |
| 884 | drawer |
| 930 | mobile medical workstation |
| 934 | lower base |
| 935 | battery |
| 939 | vertically extending post member |
| 944 | horizontal work surface |
| 952 | keyboard tray |
| 960 | vital signs monitor |
| 964 | hard drive |
| 984 | drawer |
| 1200 | mobile medical workstation |
| 1203 | WiFi wireless connection |
| 1204 | hospital network |
| 1208 | web server |
| 1212 | network software application package |
| 1216 | remote PC station |
| 1217 | viewing software |
| 1220 | Health Information Systems (Electronic Medical Record) database |
| 1300 | mobile medical workstation |
| 1304 | hospital network |
| 1308 | vital signs collector |
| 1312 | infusion pump |
| 1316 | medical device |
| 1320 | medical device |
| 1330 | server |
| 1334 | PC station |
| 1338 | Health Information Systems |
| 1400 | mobile medical workstation |
| 1406 | computing device |
| 1408 | barcode scanner |
| 1412 | digital scale |
| 1418 | ECG monitoring assembly |
| 1430 | vital signs collector |
| 1434 | wireless access point |
| 1438 | Ethernet connection |
| 1442 | CIS/EMR |
| 1450 | Hospital LAN |
| 1454 | computing station |
| 1458 | PC |
| 1462 | tablet PC |
| 1463 | devices |
| 1464 | firewall |
| 1466 | web server |
| 1470 | application servers |
| 1474 | SQL Server Cluster |
| 1476 | HIS/EMR |

It will be readily apparent to one of adequate skill that there are numerous variations and modifications that embody the inventive concepts which have been described herein as referred to in the following claims.

The invention claimed is:

1. An integrated apparatus for use in a patient encounter, said apparatus comprising:
at least one medical diagnostic instrument including a vital signs monitoring device for measuring various physiological parameters of a patient, said physiological parameters including blood pressure, glucose, body temperature, pulse rate and blood oxygen saturation; and
a computing device connected to said at least one medical diagnostic instrument, wherein at least one of said computing device and said at least one medical diagnostic instrument are programmed to detect changes in a patient condition based on changes in two or more parameters of said patient and in which said computing device is programmed to alert the user that changes in said patient condition have exceeded at least one predetermined threshold, and
in which the changes in said at least two physiological parameters are used by said computing device to predict the onset of sepsis, wherein said computing device is programmed to calculate a glycemic control score of a patient based on historical data and to determine whether a patient's blood sugar level is within a predetermined range.

2. An integrated apparatus as recited in claim 1, wherein said computing device is programmed to perform an independent determination as to whether the patient has had an infection.

3. An integrated apparatus as recited in claim 2, wherein the computing device is programmed to make a further determination to whether the patient has at least two signs of Systemic Inflammatory Response Syndrome (SIRS) if the existence of a known or suspected infection has been determined.

4. An integrated apparatus as recited in claim 3, wherein the computing device is programmed to make a determination as to whether at least one organ of the patient is failing or dysfunctional if at least two signs of SIRS have been identified.

5. An integrated apparatus for use in a patient encounter, said apparatus comprising:
- at least one medical diagnostic instrument including a vital signs monitoring device for measuring various physiological parameters of a patient, said physiological parameters including blood pressure, glucose, body temperature, pulse rate and blood oxygen saturation; and
- a computing device connected to said at least one medical diagnostic instrument, wherein at least one of said computing device and said at least one medical diagnostic instrument are programmed to detect changes in a patient condition based on changes in two or more parameters of said patient and in which said computing device is programmed to alert the user that changes in said patient condition have exceeded at least one predetermined threshold, and
- in which the changes in said at least two physiological parameters are used by said computing device to predict the onset of sepsis, wherein said apparatus is programmed to determine a first control score based on a first parameter and a second alert score based on at least a second parameter.

6. An integrated apparatus as recited in claim 5, wherein said first control score is based on the patient's blood sugar level.

7. An integrated apparatus as recited in claim 5, wherein said first control score is used to determine said second alert score in which said computing device is programmed to alert a user of said apparatus if the alert score exceeds a predetermined value.

* * * * *